United States Patent
Moreaux et al.

(10) Patent No.: US 10,662,481 B2
(45) Date of Patent: May 26, 2020

(54) METHODS FOR PREDICTING RESPONSE TO HDACI/DNMTI COMBINATION IN MULTIPLE MYELOMA

(71) Applicants: INSERM (INSTITUT NATIONAL DE LA SANTÉ ET DE LA RECHERCHE MÉDICALE), Paris (FR); UNIVERSITE DE MONTPELLIER, Montpellier (FR); CENTRE HOSPITALIER UNIVERSITAIRE DE MONTPELLIER, Montpellier (FR)

(72) Inventors: Jérôme Moreaux, Montpellier (FR); Bernard Klein, Montpellier (FR)

(73) Assignees: INSERM (INSTITUT NATIONAL DE LA SANTE ET DE LA RECHERCHE MEDICALE), Paris (FR); UNIVERSITE DE MONTPELLIER, Montpellier (FR); CENTRE HOSPITALIER UNIVERSITAIRE DE MONTPELLIER, Montpellier (FR)

( * ) Notice: Subject to any disclaimer, the term of this patent is extended or adjusted under 35 U.S.C. 154(b) by 330 days.

(21) Appl. No.: 15/127,803

(22) PCT Filed: Mar. 20, 2015

(86) PCT No.: PCT/EP2015/055992
§ 371 (c)(1),
(2) Date: Sep. 21, 2016

(87) PCT Pub. No.: WO2015/140321
PCT Pub. Date: Sep. 24, 2015

(65) Prior Publication Data
US 2017/0096710 A1    Apr. 6, 2017

(30) Foreign Application Priority Data

Mar. 21, 2014    (EP) ........................... 14305404

(51) Int. Cl.

| | |
|---|---|
| *G01N 33/48* | (2006.01) |
| *C12Q 1/6886* | (2018.01) |
| *G16B 40/00* | (2019.01) |
| *A61K 31/706* | (2006.01) |
| *A61K 31/165* | (2006.01) |
| *A61K 45/06* | (2006.01) |
| *G16H 50/30* | (2018.01) |
| *G16H 10/20* | (2018.01) |
| *A61K 31/167* | (2006.01) |
| *G06F 19/00* | (2018.01) |
| *G06G 7/58* | (2006.01) |

(52) U.S. Cl.
CPC .......... *C12Q 1/6886* (2013.01); *A61K 31/165* (2013.01); *A61K 31/167* (2013.01); *A61K 31/706* (2013.01); *A61K 45/06* (2013.01); *G06F 19/325* (2013.01); *G16B 40/00* (2019.02); *G16H 10/20* (2018.01); *G16H 50/30* (2018.01); *C12Q 2600/106* (2013.01); *C12Q 2600/158* (2013.01)

(58) Field of Classification Search
None
See application file for complete search history.

(56) References Cited

FOREIGN PATENT DOCUMENTS

WO    2014/056928 A1    4/2014

OTHER PUBLICATIONS

Smith, Emma M. et al., "The potential role of epigenetic therapy in multiple myeloma," British Journal of Haematology, 148, pp. 702-713, Nov. 13, 2009.
Heller, Gerwin et al., "Genome-Wide Transcriptional Response to 5-Aza2'-Deoxycytidine and Trichostatin A in Multiple Myeloma Cells," Cancer Res 2008; 68 (1), Jan. 1, 2008, pp. 44-54.
Moreaux, Jérôme et al., "A high-risk signature for patients with multiple myeloma established from the molecular classification of human myeloma cell lines," Haematologica, 2011; 96(4), pp. 574-582.
Moreaux, Jérôme et al., "Development of Gene Expression-Based Score to Predict Sensitivity of Multiple Myeloma Cells to DNA Methylation Inhibitors," Molecular Cancer Therapeutics; 11(12), Dec. 2012, pp. 1-8.
Fermand, J.-P. et al., "13th International Myeloma Workshop," Paris, France, May 3-6, 2011, Journal of the European Hematology Association.

(Continued)

*Primary Examiner* — Eric S Dejong
(74) *Attorney, Agent, or Firm* — Young & Thompson

(57) ABSTRACT

The present invention relates to a method of testing whether a patient suffering from multiple myeloma will respond or not to a combination treatment consisting of at least one histone deacetylase inhibitor (HDACi) with at least one DNA methyltransferase inhibitors (DNMTi) comprising: i) determining the expression level (ELi) of several genes $G_1$-$G_n$ selected from table A in a biological sample obtained from said patient ii) comparing the expression level (ELi) determined at step i) with a predetermined reference level (ELRi) iii) calculating the HADMS score trough the following formula (I) wherein βi represent the regression β coefficient reference value for the gene Gi and Ci=1 if the expression of the gene Gi (ELi) is higher than the predetermined reference level (ELRi) or Ci=−1 if the expression of the gene (ELi) is lower than or equal to the predetermined reference level (ELRi) iv) comparing the score HADMS determined at step iii) with a predetermined reference value $HADMS_R$ v) and concluding that the patient will respond to the combination treatment when the HADMS score is higher than the predetermined reference value $HADMS_R$ or concluding that the patient will not respond to the combination treatment when the HADMS score is lower than the predetermined reference value $HADMS_R$.

Figure 1:
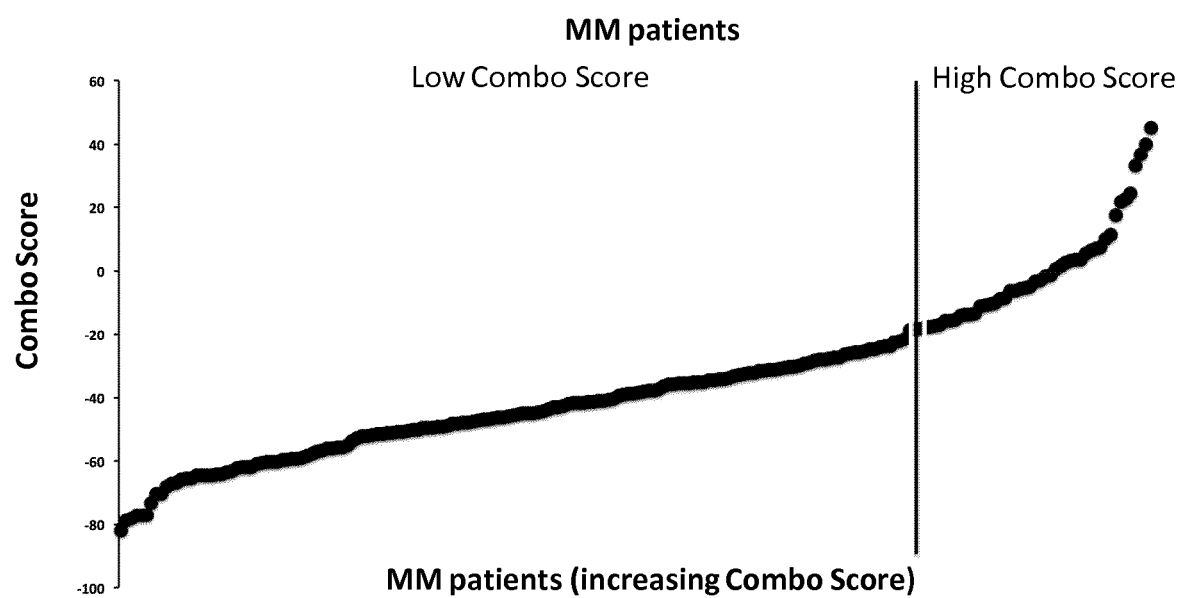

$$HADMS = \sum_{i=1}^{n} \beta i \times Ci \qquad (I)$$

8 Claims, 7 Drawing Sheets

(56) References Cited

OTHER PUBLICATIONS

Barlogie, Bart et al., "Total therapy 2 without thalidomide in comparison with total therapy 1: role of intensified induction and posttransplantation consolidation therapies," Blood, Apr. 1, 2006, vol. 107, No. 7, pp. 2633-2638.
Walker, Brian A. et al., "Aberrant global methylation patterns affect the molecular pathogenesis and prognosis of multiple myeloma," Blood, Jan. 13, 2011, vol. 117, No. 2, pp. 553-562.
Mocciaro, Annamaria and Schiebel, Elmar, "Cdc14: a highly conserved family of phosphatases with non-conserved functions," Journal of Cell Science 123, pp. 2867-2876, 2010.
Subramanian, Aravind et al., "Gene set enrichment analysis: A knowledge-based approach for interpreting genome-wide expression profiles," PNAS, Oct. 25, 2005, vol. 102, No. 42, pp. 15545-15550.
Chaidos, Aristedis et al., "Clinical drug resistance linked to interconvertible phenotypic and functional states of tumor-propagating cells in multiple myeloma," Blood, Jan. 10, 2013, vol. 121, No. 121, pp. 318-328.
Richardson, Paul G. et al., "PANORAMA 2: panobinostat in combination with bortezomib and dexamethasone in patients with relapsed and bortezomin-refractory myeloma," Blood, Aug. 15, 2013.
Moreaux, J. et al., "Gene expression-based prediction of myeloma cell sensitivity to histone deacetylase inhibitors," British Journal of Cancer, 2013, pp. 1-10.
Mateos, Maria V. et al., "Methylation is an inactivating mechanism of the p16 gene in multiple myeloma associated with high plasma cell proliferation and short survival," British Journal of Haematology, 2002, 118, pp. 1034-1040.
Khan, S. B. et al., "Analysis of histone daecetylase inhibitor, depsipeptide (FR901228), effect on multiple myeloma," British Journal of Haematology, 125, pp. 156-161, 2004.
Neri, Paola et al., "In vivo anti-myeloma activity and modulation of gene expression profile induced by valproic acid, a histone daecetylase inhibitor," British Journal of Haematology, 143, pp. 520-531, 2008.
Moreaux, J. et al. "DNA methylation score is predictive of myeloma cell sensitivity to 5-azacitidine," British Journal of Haematology, 2013.
Leung-Hagesteijn, Chungyee et al., "Xbp1s-Negative Tumor B Cells and Pre-Plasmablasts Mediate Therapeutic Proteasome Inhibitor Resistance in Multiple Myeloma," Cancer Cell, 24, pp. 289-304, Sep. 9, 2013.
Orlowski, Robert Z., "Why Proteasome Inhibitors Cannot ERADicate Multiple Myeloma," Cancer Cell, 24, pp. 275-277, Sep. 9, 2013.
Juergens, Rosalyn A., et al., "Combination Epigenetic Therapy Has Efficacy in Patients with Refractory Advanced Non-Small Cell Lung Cancer," Cancer Discovery, 2011; 1:598-607.
Maes, Ken et al., "Epigenetic Modulating Agents as a New Therapeutic Approach in Multiple Myeloma," Cancers, 2013, 5, 430-461.
Matthews, GM et al., "Preclinical screening of histone deacetylase inhibitors combined with ABT-737, rhTRAIL/MD5-1 or 5-azacytidine using syngeneic Vk*MYC multiple myeloma," Cell Death and Disease (2013), 4, pp. 1-14.
Heuck, Christoph J. et al., "Myeloma is Characterized by Stage-Specific Alteration in DNA Methylation That Occur Early during Myelomagenesis," Journal of Immunology, 2013; 190:2966-2975.
Bots, Michael and Johnstone, Ricky W., "Rational Combinations Using HDAC Inhibitors," Clinical Cancer Research, 2009;15:3970-3977.
Mitsiades, Constantine S. et al., "Transcriptional signature of histone daecetylase inhibition in multiple myeloma: Biological and clinical implications," PNAS, Jan. 13, 2004, vol. 101, No. 2, pp. 540-545.
Moreno-Bost, Amberly et al., "Epigenetic modulation of MAGE-A3 antigen expression in multiple myeloma following treatment with the demethylation agent 5-azacitidine and the histone deacetlyase inhibitor MGC0103," Cytotherapy, 2010, pp. 1-11.

Takada, S. et al., "Methylation status of fragile histidine triad (FHIT) gene and its clinical impact on prognosis of patients with multiple myeloma," European Journal of Haematology, 2005: 75; pp. 505-510.
Neri, Paola et al., "Panobinostat for the treatment of multiple myeloma," Expert Opinion on Investigational Drugs, 2012, pp. 1-15.
Cui, Xiangqin and Churchill, Gary A., "Statistical test for differential expression in cDNA microarray experiments," Genome Biology, 2003, 4:210.
Ferby, Ingvar et al., "Mig6 is a negative regulator of EGF receptor-mediated skin morphogenesis and tumor formation," Nature Medicine, vol. 12, No. 5, May 2006, pp. 568-574.
Kaiser, Martin et al., "The effects of the histone deacetylase inhibitor valproic acid on cell cycle, growth suppression and apoptosis in multiple myeloma," Haematologica 2006; 91:248-251.
Hose, Dirk et al., "Proliferation is a central independent prognostic factor and target for personalized and risk-adapted treatment in multiple myeloma," Haematologica 2011; 96(1), pp. 87-95.
Kassambara, Alboukadel et al., "Genes with a spike expression are clustered in chromosome (sub)bands and spike (sub)bands have a powerful prognostic value in patients with multiple myeloma," Haematologica 2012: 97(4), pp. 622-630.
Ying, Haoqiang et al., "Mig-6 controls EGFR trafficking and suppresses gliomagenesis," PNAS, Apr. 13, 2010, vol. 107, No. 15, pp. 6912-6917.
Braggio, Esteban et al., "Methylation status of nine tumor suppressor genes in multiple myeloma," International Journal of Hematology, 2010, 91:87-96.
Decaux, Olivier et al., "Prediction of Survival in Multiple Myeloma Based on Gene Expression Profiles Reveals Cell Cycle and Chromosomal Instability Signatures in High-Risk Patients and Hyperdiploid Signatures in Low-Risk Patients: A Study of the Intergroupe Francophone du Myelome," Journal of Clinical Oncology, vol. 26, No. 24, Aug. 20, 2008, pp. 1-21.
Tarte, Karin et al., "Induced Expression of B7-1 on Myeloma Cells Following Retroviral Gene Transfer Results in Tumor-Specific Recognition by Cytotoxic T Cells," Journal of Immunology, 1999; 163:514-524.
Jourdan, Michel et al., "Characterization of a Transitional Preplasmablast Population in the Process of Human B Cell to Plasma Cell Differentiation," Journal of Immunology, 2011: 187: 3931-3941.
Minami, J. et al., "Histone deacetylase 3 as a novel therapeutic target in multiple myeloma," Leukemia (2014), 28, pp. 680-689.
De Vos, John et al., "Comparison of gene expression profiling between malignant and normal plasma cells with oligonucleotide arrays," Oncogene (2002), 21, pp. 6848-6857.
San-Miguel, J.F. et al., "Phase Ib Study of Panobinostat and Bortezomib in Relapsed or Relapsed and Refractory Multiple Myeloma," Journal of Clinical Oncology, vol. 31, No. 29, Oct. 10, 2013, pp. 3696-3710.
Ichimura, K. et al., "1p36 is a preferential target of chromosome 1 deletions in astrocytic tumours and homozygously deleted in a subset of glioblastomas," Oncogene (2008), 27, pp. 2097-2108.
Mahtouk, K. et al., "Expression of EGF-family receptors and amphiregulin in multiple myeloma. Amphiregulin is a growth factor for myeloma cells," Oncogene (2005), 24, pp. 3512-3524.
Dimopoulos, Meletios et al., "Vorinostat or placebo in combination with bortezomib in patients with multiple myeloma (VANTAGE 088): a multicentre, randomised, double-blind study," Lancet Oncology, 2013; 14:1129-1140.
Catley, Laurence et al., "NVP-LAQ824 is a potent novel histone deacetylase inhibitor with significant activity against multiple myeloma," Blood, Oct. 1, 2003, vol. 102, No. 7, pp. 2615-2622.
Lavelle, Donald et al., "Histone Deacetylase Inhibitors Increase p21WAF1 and Induce Apoptosis of Human Myeloma Cell Lines Independent of Decreased IL-6 Receptor Expression," American Journal of Hematology 68:170-178 (2001).
Gu, Z-J et al., "Agonist anti-gp130 transducer monoclonal antibodies are human myeloma cell survival and growth factors," Leukemia (2000) 14, 188-197.

(56) References Cited

OTHER PUBLICATIONS

Wei, Zhubo et al., "Early-Onset Aging and Defective DNA Damage Response in Cdc14b-Deficient Mice," Molecular and Cellular Biology, vol. 31, No. 7, Apr. 2011, pp. 1470-1477.
Harris, Michael E. et al., "Regulation of Histone mRNA in the Unpertubed Cell Cycle Evidence Suggesting Control at Two Post-transcriptional Steps," Molecular and Cellular Biology, vol. 11, No. 5, May 1991, pp. 2416-2424.
Cedar, Howard and Bergman, Yehudit, "Linking DNA methylation and histone modification: patterns and paradigms," Nature Reviews Genetics, vol. 10, May 2009, pp. 295-304.
Mitsiades, Nicholas et al., "Molecular sequelae of histone deacetylase inhibition in human malignant B cells," Blood, May 15, 2003, vol. 101, No. 10, pp. 4055-4062.
Zhang, Xuewu et al., "Inhibition of the EGF Receptor by Binding to an Activating Kinase Domain Interface," Nature, Nov. 29, 2007; 450(7170), pp. 741-744.
Mahtouk, K. et al., "Heparan sulphate proteoglycans are essential for the myeloma cell growth activity of EGF-family ligands in multiple myeloma," Oncogene (2006) 25, 7180-7191.
Hollenbach, Paul W. et al., "A Compression of Azacitidine and Decitabine Activities in Acute Myeloid Leukemia Cell Lines," PloS ONE, Feb. 2010, vol. 5, Issue 2, pp. 1-10.
Anastasi, S. et al., "The evolutionarily conserved EBR module of RALT/MIG6 mediates suppression of the EGFR catalytic activity," Oncogene (2007) 26, pp. 7833-7846.
Guillamot, M. et al., "Cdc14b regulates mammalian RNA polymerase II and represses cell cycle transcription," Scientific Reports, 2011, 1:189, pp. 1-7.
Anastasi, Sergio et al., "Loss of RALT/MIG-6 expression in ERBB-amplified breast carcinomas enhancees ErbB-2 oncogenic potency and favors resistance to Herceptin," Oncogene (2005) 24, 4510-4548.
Xie, Bushan et al., "The mitogen-inducible gene-6 is involved in regulation of cellular senescence in normal diploid fibroblasts," Biology of the Cell (2013), 105, 488-499.
Hideshima, T. et al., "Induction of differential apoptotic pathways in multiple myeloma cells by class selective histone deacetylase inhibitors," Leukemia, accepted article preview, Oct. 22, 2013.
Zhang, XG et al., "Reproducible obtaining of human myeloma cell lines as a model for tumor stem cell study in human multiple myeloma," Blood, vol. 83, No. 12, 1994, pp. 3654-3663.
Mahtouk, K. et al., "An inhibitor of the EGF receptor family blocks myeloma cell growth factor activity of HB-EGF and potentiates dexamethasone or anti-IL-6 antibody-induced apoptosis," Blood, Mar. 1, 2004, vol. 103, No. 5, pp. 1829-1837.
Zhan, Fenghuang et al., "The molecular classification of multiple myeloma," Blood, Sep. 15, 2006, vol. 108, No. 6, pp. 2020-2028.
Shaughnessy, John D. et al., "A validated gene expression model of high-risk multiple myeloma is defined by deregulated expression of genes mapping to chromosome 1," Blood, Mar. 15, 2007, vol. 109, No. 6, pp. 2276-2284.
Xiong, Wei et al., "An analysis of the clinical and biologic significance of TP53 loss and the identification of potential novel transcription targets of TP53 in multiple myeloma," Blood, Nov. 15, 2008, vol. 112, No. 10, pp. 4235-4246.
Fandy, Tamer E. et al., "Early epigenetic changes and DNA damage do not predict clinical response in an overlapping schedule of 5-azacytidine and entinostat in patients with myeloid malignancies," Blood, Sep. 24, 2009, vol. 114, No. 13, pp. 2764-2773.
Jourdan, Michel et al., "An in vitro model of differentiation of memory B cells into plasmablasts and plasma cells including detailed phenotypic and molecular characterization," Blood, Dec. 10, 2009, vol. 114, No. 25, pp. 5173-5181.
Reme, Thierry et al., "Modeling risk stratification in human cancer," Bioinformatics, vol. 29, No. 9, 2013, pp. 1149-1157.
Rebouissou, Cosette et al., "A gp130 Interleukin-6 Transducer-Dependent SCID Model of Human Multiple Myeloma," Blood, vol. 91, No. 12, 1998, pp. 4727-4737.
Zhange, Q-L et al., "The proteasome inhibitor bortezomib interacts synergistically with the histone deacetylase inhibitor suberoylanilide hydroxamic acid to induce T-leukemia/lymphoma cells apoptosis," Leukemia (2009) 23, pp. 1507-1514.
Communication under Rule 71(3) EPC in European Patent Application No. 15 741 765.0 dated Jul. 30, 2019.

METHODS FOR PREDICTING RESPONSE TO HDACI/DNMTI COMBINATION IN MULTIPLE MYELOMA

FIELD OF THE INVENTION

The present invention relates to methods for predicting multiple myeloma treatment response.

BACKGROUND OF THE INVENTION

Multiple myeloma (MM) is an almost fatal neoplasia characterized by the accumulation of malignant plasma cells (MMC) in the bone marrow. The profile of DNA methylation in MM comprises genomic global hypomethylation and simultaneous promoter hypermethylation of known or potential tumor suppressor genes (Heuck, 2013; Walker, 2010). Recently, hypermethylation of several potential suppressor genes was demonstrated to be associated with significantly shorter overall survival (Heuck, 2013).

Decitabine (5-aza-2'-deoxycytidine) or 5-azacytidine are both clinically used DNMT inhibitors for the treatment of myelodysplastic syndrome (MDS) and acute myelogenous leukemia (AML) (Hollenbach, 2010). In MM, clinical trials are ongoing with DNMTi as monotherapy or combined with lenalidomide or dexamethasone (Maes, 2013). Histone deacetylases (HDAC) represent also molecular targets for the treatment of different cancers including MM (Feng, 2008; Khan, 2004; Lavelle, 2001; Mitsiades, 2004; Mitsiades, 2003; Catley, 2003; Kaiser, 2006; Neri, 2012; Neri, 2008; Minami, 2013; Hideshima, 2013). Romidepsin and Vorinostat (SAHA) have been approved by the Food and Drug Administration (FDA) for the treatment of cutaneous T-cell lymphoma (Zhang, 2009) and several HDACi are evaluated in clinical trials in MM (Maes, 2013; Neri, 2012). Proteasome inhibition leading to accumulation of ubiquitinated proteins, affecting unfolded protein response (UPR) and increasing HDAC-mediated aggregosome formation indicated that HDACi and bortezomib combination could be promising in MM (Richardson, 2013; San-Miguel, 2013). Combination of panobinostat/bortezomib/dexamethasone (PANORAMA) and of vorinostat/bortezomib (VANTAGE 088) have been initiated in two large phase III clinical trials (Richardson, 2013; Dimopoulos, 2013). Results of VANTAGE 088 trial shown that association of vorinostat and bortezomib prolonged significantly progression free survival, compared to bortezomib and placebo, in patients with relapsed or refractory MM (Dimopoulos, 2013). However, this combination is associated with toxicity and new treatment schedules should be investigated to increase tolerability and enhance efficacy (Dimopoulos, 2013).

It was reported that HDACi and DNMTi treatment can induce MAGE-A3 in MM, an attractive target for immunotherapy, and facilitate killing by MAGE-A3 specific cytotoxic T lymphocytes (Moreno-Bost, 2011). Recently, Matthews et at investigated the potential of combining HDACi with a BH3-only mimetic (ABT-737), recombinant human TNF-related apoptosis-inducing ligand (rhTRAIL) or 5-azacitidine, in vivo, using the Vk*MYC transgenic MM mouse model (Matthews, 2013). HADCi/rhTRAIL or HDACi/ABT-737 combinations are associated with important drug induced toxicity in vivo. In contrast, HDACi and DNMTi demonstrated a significant reduction of tumor load in vivo and prolonged survival of mice without toxicity (Matthews, 2013). In patients with solid cancers or advanced haematological malignancies, HDACi and DNMTi combination was well tolerated (Bots, 2009) and suggested promising activity in MDS, AML (Bots, 2009; Fandy, 2009; Zhang, 2009) and refractory advanced non-small cell lung cancer (Juergens, 2011). Together, these observations suggest that targeting the aberrant tumor-specific epigenetic program with DNMTi and HDACi treatment could have therapeutic interest in MM. However, identification of biomarkers predictive for sensitivity of MMCs to epigenetic therapies remains an important objective to improve clinical trials. The inventors recently reported gene expression (GEP)-based risk scores to predict the sensitivity of MMC to DNMTi (Moreaux, 2013; Moreaux, 2012) and HDACi (Moreaux, 2013). Since HDACi and DNMTi combination have potential therapeutic value in MM, the inventors searched to build a GEP-based score that could be useful to conduct epigenetic-targeted combination trials.

The identification of biomarkers predictive for sensitivity of MMCs to HDACi and DNMTi combination is an important objective for optimizing these clinical trials. In the present invention, the inventors used gene expression profiling of Multiple Myeloma Cells (MMCs) to build a novel "HDACi/DNMTi score" or "HADMS" that makes it possible identification of patients whose MMCs will be targeted by a combination treatment consisting of at least one DNA methyltransferase inhibitor (DNMTi) with at least one histone deacetylase inhibitor (HDACi).

SUMMARY OF THE INVENTION

The present invention relates to a method of testing whether a patient suffering from multiple myeloma will respond or not to a combination treatment consisting of at least one DNA methyltransferase inhibitor (DNMTi) with at least one histone deacetylase inhibitor (HDACi).

DETAILED DESCRIPTION OF THE INVENTION

The multiple myeloma treatment response was investigated by the inventors using histone deacetylase inhibitor (HDACi), DNA methyltransferase inhibitors (DNMTi), human multiple myeloma cell lines (HMCLs) and primary multiple myeloma cells of patients.

Decitabine and TSA treatment resulted in a significant upregulation of 375 genes. Among the 375 genes, the 96 genes building the histone acetylation/DNA methylation score (HADM score or HADMS), include 42 genes associated with a bad prognostic value and 54 genes associated with a good prognosis in a cohort of 206 newly-diagnosed patients (HM cohort). Using maxstat analysis for overall survival, HADM score was significantly associated with high-risk myeloma in the 2 independent patients' cohorts, HM and UAMS-TT2. The inventors reported a new gene expression-based score to predict the myeloma cell sensitivity to a combination treatment consisting of at least one DNA methyltransferase inhibitor (DNMTi) with at least one histone deacetylase inhibitor (HDACi). HADM score allows identification of high-risk patients associated with MMC's higher sensitivity to a combination treatment consisting of at least one DNA methyltransferase inhibitor (DNMTi) with at least one histone deacetylase inhibitor (HDACi), which is useful in identifying patients who could benefit from combination of epigenetic therapy.

Definitions

The term "patient" denotes a mammal. In a preferred embodiment of the invention, a patient refers to any patient (preferably human) afflicted with multiple myeloma. The term "multiple myeloma" refers to multiple myeloma such as revised in the World Health Organisation Classification C90.

The term "histone deacetylase inhibitor" or "HDACi" has its general meaning in the art and refers to a multiple myeloma treatment. The term "histone deacetylase inhibitor" or "HDACi" refers to histone deacetylase inhibitor that can be grouped in four classes: hydroxamates (panobinostat (LBH-589), trichostatin-A (TSA), vorinostat (SAHA), belinostat (PXD101), NVP-LAQ824 and givinostat (ITF2357)), cyclic peptide (romidepsin (depsipeptide)), aliphatic acids (valproic acid (VPA) and sodium phenylbutyrate) and benzamides (MS-275, MGCD0103) (10). HDACi are characterized as class I-specific HDACs inhibitors (MGCD0103, romidepsin and MS-275) or as pan-HDAC inhibitors, denoting activity against both classes I and II HDACs (TSA, panobinostat, vorinostat and belinostat) (10).

The term "DNA methyltransferase inhibitors" or "DNMTi" has its general meaning in the art and refers to a multiple myeloma treatment. The term "DNA methyltransferase inhibitors" or "DNMTi" refers to DNA methyltransferase inhibitor that can be sub-divided into nucleoside analogue (5-Azacytidine (azacytidine), 5-Aza-2'-deoxycytidine (decitabine, 5-Aza-CdR), zebularine, 5-Fluoro-2'-deoxycytidine (5-F-CdR), 5,6-Dihydro-5-azacytidine (DHAC)) and non-nucleoside analogue families (Hydralazine, Procainamide, Procaine, EGCG ((−)-epigallocatechin-3-gallate), Psammaplin A, MG98, RG108) (8).

The term "biological sample" refers to multiple myeloma cells, bone marrow or medullary cell.

All the genes pertaining to the invention are known per se, and are listed in the below Table A.

TABLE A

Set of predictive genes.

| Gene | Gene ID Probeset | Gene Symbol | β coefficient | Reference Level (ELRi) |
|---|---|---|---|---|
| G1 | 225842_at | — | −0.899957319 | 69 |
| G2 | 226725_at | — | 0.818731911 | 131 |
| G3 | 240979_at | — | −1.734769051 | 72 |
| G4 | 209993_at | ABCB1 | 1.014206321 | 30 |
| G5 | 205997_at | ADAM28 | −0.895564458 | 57 |
| G6 | 209122_at | ADFP | −0.943134148 | 171 |
| G7 | 206385_s_at | ANK3 | −0.86352778 | 10 |
| G8 | 225283_at | ARRDC4 | −0.942014898 | 45 |
| G9 | 201243_s_at | ATP1B1 | −1.157295661 | 102 |
| G10 | 242234_at | BIRC4BP | 1.09912532 | 103 |
| G11 | 212560_at | C11orf32 | −0.80719933 | 10 |
| G12 | 210785_s_at | C1orf38 | −0.923865573 | 138 |
| G13 | 216379_x_at | CD24 | −0.934005159 | 46 |
| G14 | 221555_x_at | CDC14B | −1.008662223 | 139 |
| G15 | 225685_at | CDC42EP3 | −0.976621995 | 92 |
| G16 | 201131_s_at | CDH1 | −0.790641274 | 3 |
| G17 | 202284_s_at | CDKN1A | −1.115018187 | 529 |
| G18 | 213348_at | CDKN1C | −1.01782728 | 35 |
| G19 | 213800_at | CFH | 0.927589961 | 46 |
| G20 | 213317_at | CLIC5 | 0.955430136 | 164 |
| G21 | 224583_at | COTL1 | −0.81118032 | 6 |
| G22 | 235700_at | CT45-2 | 0.947041492 | 22 |
| G23 | 202436_s_at | CYP1B1 | −1.036466399 | 28 |
| G24 | 208779_x_at | DDR1 | −0.947438553 | 102 |
| G25 | 222793_at | DDX58 | 0.962155444 | 133 |
| G26 | 214079_at | DHRS2 | 1.113374737 | 61 |
| G27 | 219313_at | DKFZp434C0328 | −1.005680344 | 133 |
| G28 | 221563_at | DUSP10 | 1.037759883 | 144 |
| G29 | 200878_at | EPAS1 | −1.038609726 | 127 |
| G30 | 224657_at | ERRFI1 | −0.846840786 | 25 |

TABLE A-continued

Set of predictive genes.

| Gene | Gene ID Probeset | Gene Symbol | β coefficient | Reference Level (ELRi) |
|---|---|---|---|---|
| G31 | 225328_at | FBXO32 | −1.060608582 | 184 |
| G32 | 228745_at | FLJ13611 | −1.219072077 | 57 |
| G33 | 212464_s_at | FN1 | −1.072661597 | 1 |
| G34 | 211458_s_at | GABARAPL1 | −0.96494036 | 350 |
| G35 | 231577_s_at | GBP1 | −0.865861628 | 68 |
| G36 | 226269_at | GDAP1 | 1.176392353 | 22 |
| G37 | 200696_s_at | GSN | −1.035458903 | 50 |
| G38 | 214469_at | HIST1H2AE | 1.168940874 | 87 |
| G39 | 235456_at | HIST1H2BD | 1.224250233 | 99 |
| G40 | 203932_at | HLA-DMB | −1.211306838 | 161 |
| G41 | 212998_x_at | HLA-DQB1 | −0.800807606 | 2 |
| G42 | 208894_at | HLA-DRA | −1.122412883 | 143 |
| G43 | 215193_x_at | HLA-DRB1 | −0.883817028 | 47 |
| G44 | 211538_s_at | HSPA2 | 1.029045845 | 45 |
| G45 | 202411_at | IFI27 | 1.106775525 | 185 |
| G46 | 203153_at | IFIT1 | 0.967220137 | 401 |
| G47 | 229450_at | IFIT3 | 1.241731919 | 642 |
| G48 | 205227_at | IL1RAP | −0.879498221 | 7 |
| G49 | 225525_at | KIAA1671 | 1.103510707 | 18 |
| G50 | 235252_at | KSR | −1.275100289 | 82 |
| G51 | 236565_s_at | LARP6 | 1.131704184 | 57 |
| G52 | 226702_at | LOC129607 | 0.803290573 | 723 |
| G53 | 225407_at | MBP | −0.929928327 | 10 |
| G54 | 235568_at | MCEMP1 | −0.783211082 | 50 |
| G55 | 214696_at | MGC14376 | −1.004393637 | 296 |
| G56 | 238430_x_at | MGC19764 | 0.949198229 | 85 |
| G57 | 226066_at | MITF | 0.949130851 | 164 |
| G58 | 212509_s_at | MXRA7 | −1.106064046 | 156 |
| G59 | 203215_s_at | MYO6 | −0.878410657 | 107 |
| G60 | 203413_at | NELL2 | 1.101239744 | 55 |
| G61 | 229963_at | NGFRAP1L1 | 1.205822872 | 1834 |
| G62 | 205552_s_at | OAS1 | 1.098161459 | 590 |
| G63 | 204972_at | OAS2 | 1.569325358 | 749 |
| G64 | 218543_s_at | PARP12 | 1.097562753 | 589 |
| G65 | 224701_at | PARP14 | 1.412504773 | 360 |
| G66 | 223220_s_at | PARP9 | 0.928781518 | 343 |
| G67 | 205380_at | PDZK1 | 0.944860168 | 5 |
| G68 | 217996_at | PHLDA1 | −1.065526416 | 242 |
| G69 | 203879_at | PIK3CD | −1.353529364 | 74 |
| G70 | 201939_at | PLK2 | 1.0990142 | 107 |
| G71 | 202430_s_at | PLSCR1 | 1.260332375 | 301 |
| G72 | 203680_at | PRKAR2B | −0.966689497 | 24 |
| G73 | 202252_at | RAB13 | −1.308103119 | 248 |
| G74 | 230233_at | RASGEF1B | −1.145228745 | 66 |
| G75 | 242625_at | RSAD2 | 0.993659251 | 89 |
| G76 | 34408_at | RTN2 | −1.251325387 | 90 |
| G77 | 210592_s_at | SAT | −1.011124683 | 1916 |
| G78 | 204030_s_at | SCHIP1 | −1.020819238 | 21 |
| G79 | 210432_s_at | SCN3A | 1.158531601 | 21 |
| G80 | 201427_s_at | SEPP1 | −1.053836286 | 447 |
| G81 | 228726_at | SERPINB1 | −1.143171879 | 75 |
| G82 | 209723_at | SERPINB9 | −0.80370612 | 75 |
| G83 | 205352_at | SERPINI1 | 1.274785788 | 305 |
| G84 | 226728_at | SLC27A1 | −0.93950361 | 94 |
| G85 | 216236_s_at | SLC2A14 | −0.949244583 | 48 |
| G86 | 202497_x_at | SLC2A3 | −1.029814297 | 12 |
| G87 | 209762_x_at | SP110 | 1.463775754 | 318 |
| G88 | 210394_x_at | SSX4 | 0.934669303 | 102 |
| G89 | 209969_s_at | STAT1 | 1.014749908 | 394 |
| G90 | 206118_at | STAT4 | 0.948161655 | 270 |
| G91 | 202085_at | TJP2 | −1.12983309 | 25 |
| G92 | 223949_at | TMPRSS3 | 0.962769445 | 10 |
| G93 | 213423_x_at | TUSC3 | 0.786424757 | 56 |
| G94 | 219211_at | USP18 | 1.144102267 | 188 |
| G95 | 228617_at | XAF1 | 1.175253328 | 686 |
| G96 | 219062_s_at | ZCCHC2 | −0.984374978 | 11 |

Methods for Predicting Response

The present invention relates to a method of testing whether a patient suffering from multiple myeloma will respond or not to a combination treatment consisting of at least one histone deacetylase inhibitor (HDACi) with at least one DNA methyltransferase inhibitor (DNMTi) comprising:

i) determining the expression level (ELi) of several genes $G_1$-$G_n$ selected from table A in a biological sample obtained from said patient ii) comparing the expression level (ELi) determined at step i) with a predetermined reference level (ELRi)

iii) calculating the HADMS score trough the following formula $$HADMS = \sum_{i=1}^{n} \beta i \times Ci$$

wherein βi represent the regression β coefficient reference value for the gene $G_i$ and Ci=1 if the expression of the gene $G_i$ (ELi) is higher than the predetermined reference level (ELRi) or Ci=−1 if the expression of the gene (ELi) is lower than or equal to the predetermined reference level (ELRi)

iv) comparing the score HADMS determined at step iii) with a predetermined reference value $HADMS_R$ v) and concluding that the patient will respond to the combination treatment when the HADMS score is higher than the predetermined reference value $HADMS_R$ or concluding that the patient will not respond to the combination treatment when the HADMS score is lower than the predetermined reference value $HADMS_R$.

In some embodiments, the expression levels of at least 42 genes from Table A are determined wherein said genes are: EPAS1, ATP1B1, TJP2, RAB13, IFI27, PLSCR1, CYP1B1, SLC2A3, IFIT1, SCHIP1, PDZK1, DDR1, HLA-DRA, SERPINB9, SP110, SSX4, C1orf38, FN1, MXRA7, CLIC5, HIST1H2AE, MGC14376, HLA-DRB1, SLC2A14, USP18, DKFZp434C0328, CDC14B, DDX58, PARP9, TMPRSS3, COTL1, PARP14, KIAA1671, GDAP1, LOC129607, SLC27A1, FLJ13611, KSR, HIST1H2BD, 240979_at EST, BIRC4BP and RSAD2.

In some embodiment, the expression levels of 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95 or 96 genes from Table A are determined wherein every combinations of genes comprises a minimal set of 42 genes consisting of: EPAS1, ATP1B1, TJP2, RAB13, IFI27, PLSCR1, CYP1B1, SLC2A3, IFIT1, SCHIP1, PDZK1, DDR1, HLA-DRA, SERPINB9, SP110, SSX4, C1orf38, FN1, MXRA7, CLIC5, HIST1H2AE, MGC14376, HLA-DRB1, SLC2A14, USP18, DKFZp434C0328, CDC14B, DDX58, PARP9, TMPRSS3, COTL1, PARP14, KIAA1671, GDAP1, LOC129607, SLC27A1, FLJ13611, KSR, HIST1H2BD, 240979_at EST, BIRC4BP and RSAD2.

In some embodiments, the expression levels of the 96 genes of Table A are determined.

Determination of the expression level of the genes can be performed by a variety of techniques. Generally, the expression level as determined is a relative expression level. More preferably, the determination comprises contacting the biological sample with selective reagents such as probes, primers or ligands, and thereby detecting the presence, or measuring the amount, of polypeptide or nucleic acids of interest originally in the biological sample. Contacting may be performed in any suitable device, such as a plate, microtiter dish, test tube, well, glass, column, and so forth. In specific embodiments, the contacting is performed on a substrate coated with the reagent, such as a nucleic acid array or a specific ligand array. The substrate may be a solid or semi-solid substrate such as any suitable support comprising glass, plastic, nylon, paper, metal, polymers and the like. The substrate may be of various forms and sizes, such as a slide, a membrane, a bead, a column, a gel, etc. The contacting may be made under any condition suitable for a detectable complex, such as a nucleic acid hybrid or an antibody-antigen complex, to be formed between the reagent and the nucleic acids or polypeptides of the biological sample.

In a preferred embodiment, the expression level may be determined by determining the quantity of mRNA.

Methods for determining the quantity of mRNA are well known in the art. For example the nucleic acid contained in the biological sample is first extracted according to standard methods, for example using lytic enzymes or chemical solutions or extracted by nucleic-acid-binding resins following the manufacturer's instructions. The extracted mRNA is then detected by hybridization (e.g., Northern blot analysis) and/or amplification (e.g., RT-PCR). Preferably quantitative or semi-quantitative RT-PCR is preferred. Real-time quantitative or semi-quantitative RT-PCR is particularly advantageous.

Other methods of amplification include ligase chain reaction (LCR), transcription-mediated amplification (TMA), strand displacement amplification (SDA) and nucleic acid sequence based amplification (NASBA).

Nucleic acids having at least 10 nucleotides and exhibiting sequence complementarity or homology to the mRNA of interest herein find utility as hybridization probes or amplification primers. It is understood that such nucleic acids need not be identical, but are typically at least about 80% identical to the homologous region of comparable size, more preferably 85% identical and even more preferably 90-95% identical. In certain embodiments, it will be advantageous to use nucleic acids in combination with appropriate means, such as a detectable label, for detecting hybridization. A wide variety of appropriate indicators are known in the art including, fluorescent, radioactive, enzymatic or other ligands (e.g. avidin/biotin).

Probes typically comprise single-stranded nucleic acids of between 10 to 1000 nucleotides in length, for instance of between 10 and 800, more preferably of between 15 and 700, typically of between 20 and 500. Primers typically are shorter single-stranded nucleic acids, of between 10 to 25 nucleotides in length, designed to perfectly or almost perfectly match a nucleic acid of interest, to be amplified. The probes and primers are "specific" to the nucleic acids they hybridize to, i.e. they preferably hybridize under high stringency hybridization conditions (corresponding to the highest melting temperature Tm, e.g., 50% formamide, 5× or 6×SCC. SCC is a 0.15 M NaCl, 0.015 M Na-citrate).

The nucleic acid primers or probes used in the above amplification and detection method may be assembled as a kit. Such a kit includes consensus primers and molecular probes. A preferred kit also includes the components necessary to determine if amplification has occurred. The kit may also include, for example, PCR buffers and enzymes; positive control sequences, reaction control primers; and instructions for amplifying and detecting the specific sequences.

In a particular embodiment, the methods of the invention comprise the steps of providing total RNAs extracted from a biological samples and subjecting the RNAs to amplification and hybridization to specific probes, more particularly by means of a quantitative or semi-quantitative RT-PCR.

In another preferred embodiment, the expression level is determined by DNA chip analysis. Such DNA chip or nucleic acid microarray consists of different nucleic acid probes that are chemically attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes comprise nucleic acids such as cDNAs or oligonucleotides that may be about 10 to about 60 base pairs. To determine the expression level, a biological sample from a test patient, optionally first subjected to a reverse transcription, is labelled and contacted with the microarray in hybridization conditions, leading to the formation of complexes between target nucleic acids that are complementary to probe sequences attached to the microarray surface. The labelled hybridized complexes are then detected and can be quantified or semi-quantified. Labelling may be achieved by various methods, e.g. by using radioactive or fluorescent labelling. Many variants of the microarray hybridization technology are available to the man skilled in the art (see e.g. the review by Hoheisel, Nature Reviews, Genetics, 2006, 7:200-210)

In this context, the invention further provides a DNA chip comprising a solid support which carries nucleic acids that are specific to the genes listed in Table A.

Predetermined reference values ELRi or $HADMS_R$ used for comparison may consist of "cut-off" values.

For example; each reference ("cut-off") value ELRi for each gene may be determined by carrying out a method comprising the steps of:

a) providing a collection of samples from patients suffering from multiple myeloma;

b) determining the expression level of the relevant gene for each sample contained in the collection provided at step a);

c) ranking the samples according to said expression level d) classifying said samples in pairs of subsets of increasing, respectively decreasing, number of members ranked according to their expression level, e) providing, for each sample provided at step a), information relating to the actual clinical outcome for the corresponding cancer patient (i.e. the duration of the disease-free survival (DFS), or the event free survival (EFS) or the overall survival (OS) or both);

f) for each pair of subsets of tumour tissue samples, obtaining a Kaplan Meier percentage of survival curve;

g) for each pair of subsets of tumour tissue samples calculating the statistical significance (p value) between both subsets h) selecting as reference value ELR for the expression level, the value of expression level for which the p value is the smallest.

For example the expression level of a gene Gi has been assessed for 100 samples of 100 patients. The 100 samples are ranked according to the expression level of gene Gi. Sample 1 has the highest expression level and sample 100 has the lowest expression level. A first grouping provides two subsets: on one side sample Nr 1 and on the other side the 99 other samples. The next grouping provides on one side samples 1 and 2 and on the other side the 98 remaining samples etc., until the last grouping: on one side samples 1 to 99 and on the other side sample Nr 100. According to the information relating to the actual clinical outcome for the corresponding cancer patient, Kaplan Meier curves are prepared for each of the 99 groups of two subsets. Also for each of the 99 groups, the p value between both subsets was calculated. The reference value ELRi is then selected such as the discrimination based on the criterion of the minimum p value is the strongest. In other terms, the expression level corresponding to the boundary between both subsets for which the p value is minimum is considered as the reference value. It should be noted that according to the experiments made by the inventors, the reference value ELRi is not necessarily the median value of expression levels.

The man skilled in the art also understands that the same technique of assessment of the $HADMS_R$ could be used for obtaining the reference value and thereafter for assessment of the response to the combination treatment of the present invention. However in one embodiment, the reference value $HADMS_R$ is the median value of HADMS.

In one embodiment, the reference value ELRi for the gene Gi is described in table A (right column).

The regression β coefficient reference values may be easily determined by the skilled man in the art for each gene Gi using a Cox model. The Cox model is based on a modeling approach to the analysis of survival data. The purpose of the model is to simultaneously explore the effects of several variables on survival. The Cox model is a well-recognised statistical technique for analysing survival data. When it is used to analyse the survival of patients in a clinical trial, the model allows us to isolate the effects of treatment from the effects of other variables. The logrank test cannot be used to explore (and adjust for) the effects of several variables, such as age and disease duration, known to affect survival. Adjustment for variables that are known to affect survival may improve the precision with which we can estimate the treatment effect. The regression method introduced by Cox is used to investigate several variables at a time. It is also known as proportional hazards regression analysis. Briefly, the procedure models or regresses the survival times (or more specifically, the so-called hazard function) on the explanatory variables. The hazard function is the probability that an individual will experience an event (for example, death) within a small time interval, given that the individual has survived up to the beginning of the interval. It can therefore be interpreted as the risk of dying at time t. The quantity h0 (t) is the baseline or underlying hazard function and corresponds to the probability of dying (or reaching an event) when all the explanatory variables are zero. The baseline hazard function is analogous to the intercept in ordinary regression (since exp0=1). The regression coefficient β gives the proportional change that can be expected in the hazard, related to changes in the explanatory variables. The coefficient β is estimated by a statistical method called maximum likelihood. In survival analysis, the hazard ratio (HR) (Hazard Ratio=exp(β)) is the ratio of the hazard rates corresponding to the conditions described by two sets of explanatory variables. For example, in a drug study, the treated population may die at twice the rate per unit time as the control population. The hazard ratio would be 2, indicating higher hazard of death from the treatment.

In one embodiment, the regression β coefficient reference values are described in Table A.

Typically, the reference value $HADMS_R$ is −21.57 for determining whether a patient suffering from multiple myeloma will respond to the combination treatment of the invention and for predicting the survival time of patient suffering from multiple myeloma.

The invention also relates to a kit for performing the methods as above described, wherein said kit comprises means for measuring the expression level of the genes listed in Table A. Typically the kit may include a primer, a set of primers, a probe, a set of probes as above described. In a particular embodiment, the probe or set of probes are labelled as above described. The kit may also contain other suitably packaged reagents and materials needed for the particular detection protocol, including solid-phase matrices, if applicable, and standards.

In a particular embodiment, the score may be generated by a computer program.

Methods of Treatment

The method of the invention allows to define a subgroup of patients who will be responsive ("responder") or not ("non responder") to the treatment with the combination treatment consisting of at least one histone deacetylase inhibitor with at least one DNA methyltransferase inhibitor.

A further object of the invention relates to a method for the treatment of multiple myeloma in a patient in need thereof.

In the context of the invention, the term "treating" or "treatment", as used herein, means reversing, alleviating, inhibiting the progress of, or preventing the disorder or condition to which such term applies, or one or more symptoms of such disorder or condition.

In a particular embodiment, the method comprises the following steps:

a) testing whether the patient will respond or not to the combination treatment of the present invention by performing the method according to the invention b) administering the combination treatment of the present invention, when the HADMS score is higher than the reference value $HADMS_R$ (i.e. the patient will respond to the combination treatment consisting of at least one histone deacetylase inhibitor with at least one DNA methyltransferase inhibitor).

A further object of the invention relates to a combination treatment consisting of at least one histone deacetylase inhibitor with at least one DNA methyltransferase inhibitor for use in the treatment of multiple myeloma in a patient in need thereof, wherein the patient was being classified as responder by the method as above described.

A further object of the invention relates to a combination treatment consisting of trichostatin-A (TSA) or vorinostat (SAHA) with decitabine (5-aza-2'-deoxycytidine) or 5-azacytidine for use in the treatment of multiple myeloma in a patient in need thereof, wherein the patient was being classified as responder by the method as above described.

The invention will be further illustrated by the following figures and examples. However, these examples and figures should not be interpreted in any way as limiting the scope of the present invention.

FIGURES

FIG. 1: Clustergram of the signals of the 96 genes used to build HADMS score in myeloma cells of 206 previously untreated patients.

The signals of the 96 probe sets in MMCs of 206 patients, ordered by increasing HADMS score, are displayed from low (deep blue) to high (deep red) expression.

Figure 2:
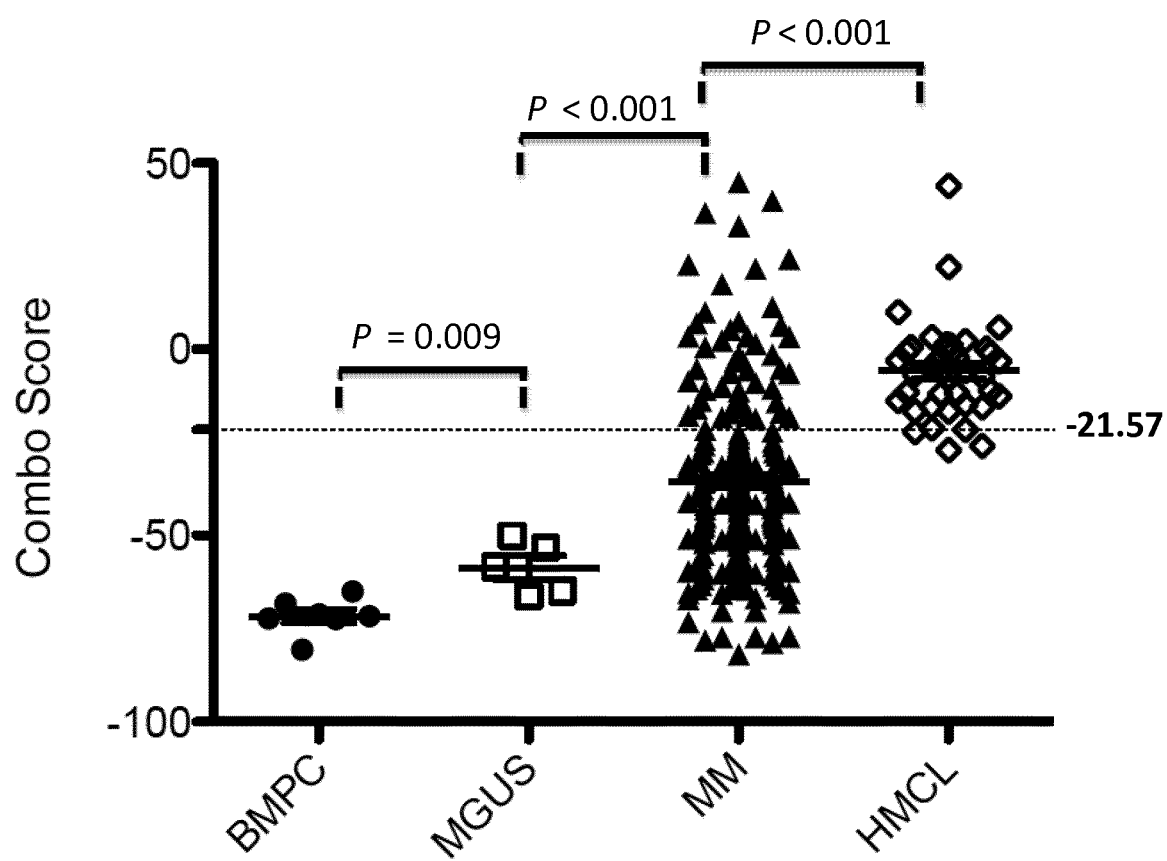

FIG. 2: HADMS score in normal and malignant plasma cells.

HADMS score in normal bone marrow plasma cells (n=7), in pre-malignant plasma cells of patients with monoclonal gammopathy of undetermined significance (MGUS, n=5), in multiple myeloma cells of patients with intramedullary MM (n=206) and in human myeloma cell lines (n=40).

FIG. 3: Prognostic value of HADMS score in multiple myeloma.

(A) Patients of the HM cohort were ranked according to increased HADMS score and a maximum difference in OS was obtained with HADMS score=−21.57 splitting patients in high risk (23.7%) and low risk (76.3%) groups. The prognostic value of HADMS score was validated using an independent cohort of 345 patients from UAMS treated with TT2 therapy (UAMS-TT2 cohort). The parameters to compute the HADMS score of patients of UAMS-TT2 cohort and the proportions delineating the 2 prognostic groups were those defined with HM cohort.

(B) The HADMS score could also predict for event free survival (EFS) in the HM and UAMS-TT2 cohorts.

Figure 4:
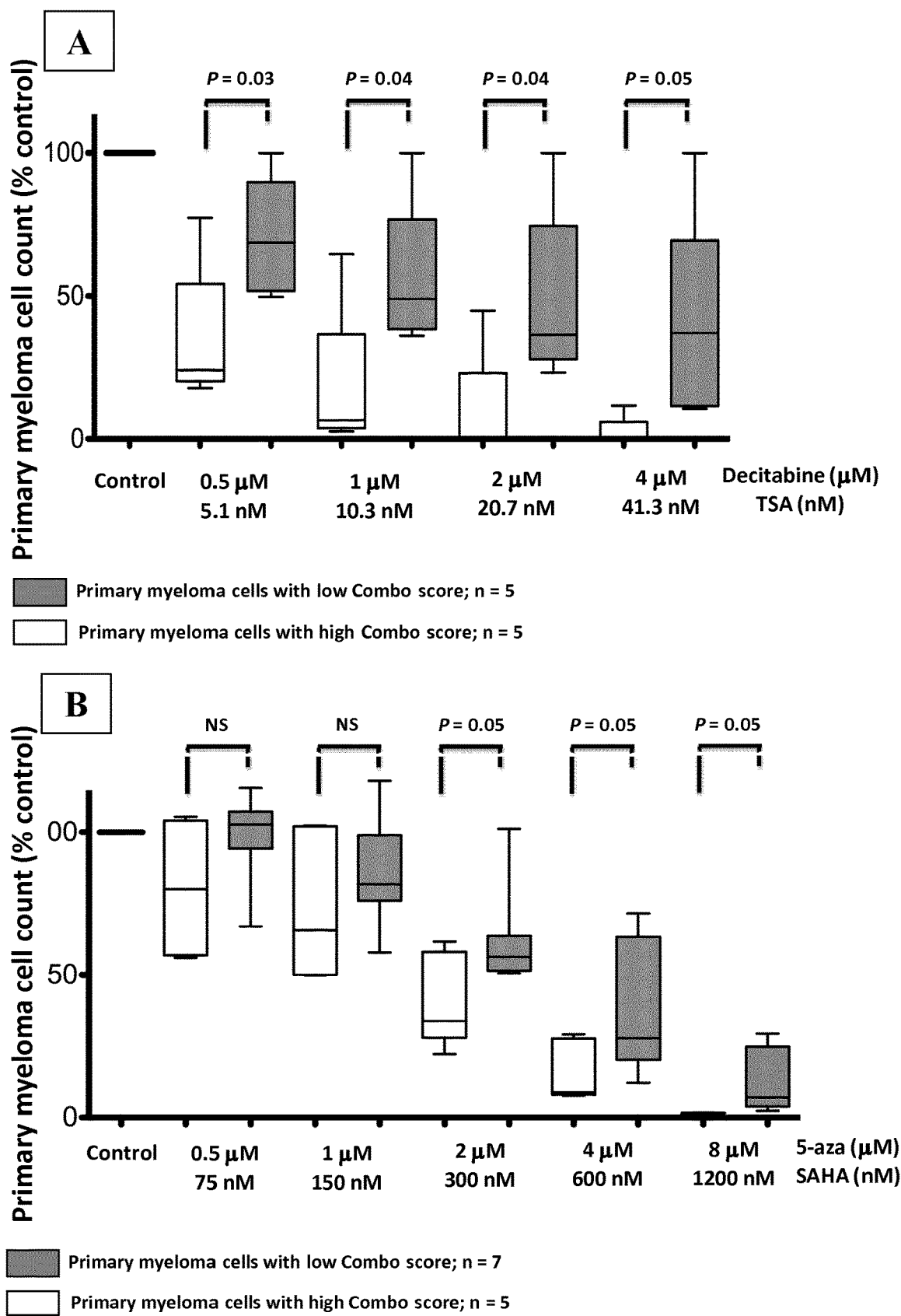

FIG. 4: HADMS score predicts for sensitivity of primary myeloma cells of patients to HDACi/DNMTi combined treatment.

(A) Mononuclear cells from tumour samples of 10 patients with MM were cultured for 4 days in the presence of IL-6 (2 ng/ml) with or without graded decitabine and TSA concentrations. At day 4 of culture, the count of viable CD138$^+$ MMCs was determined using flow cytometry. The grey columns represent the mean±SD of primary myeloma cell counts (expressed as the percentage of the count without adding drugs) of the 5 patients with a low HADMS score and the white columns that of the 5 patients with a high HADMS score.

(B) 5-azacitidine and SAHA combination was also investigated using samples of 12 myeloma patients. The grey columns represent the mean±SD of primary myeloma cell counts (expressed as the percentage of the count without adding drugs) of the 7 patients with a low HADMS score and the white columns that of the 5 patients with a high HADMS score.

Figure 5:
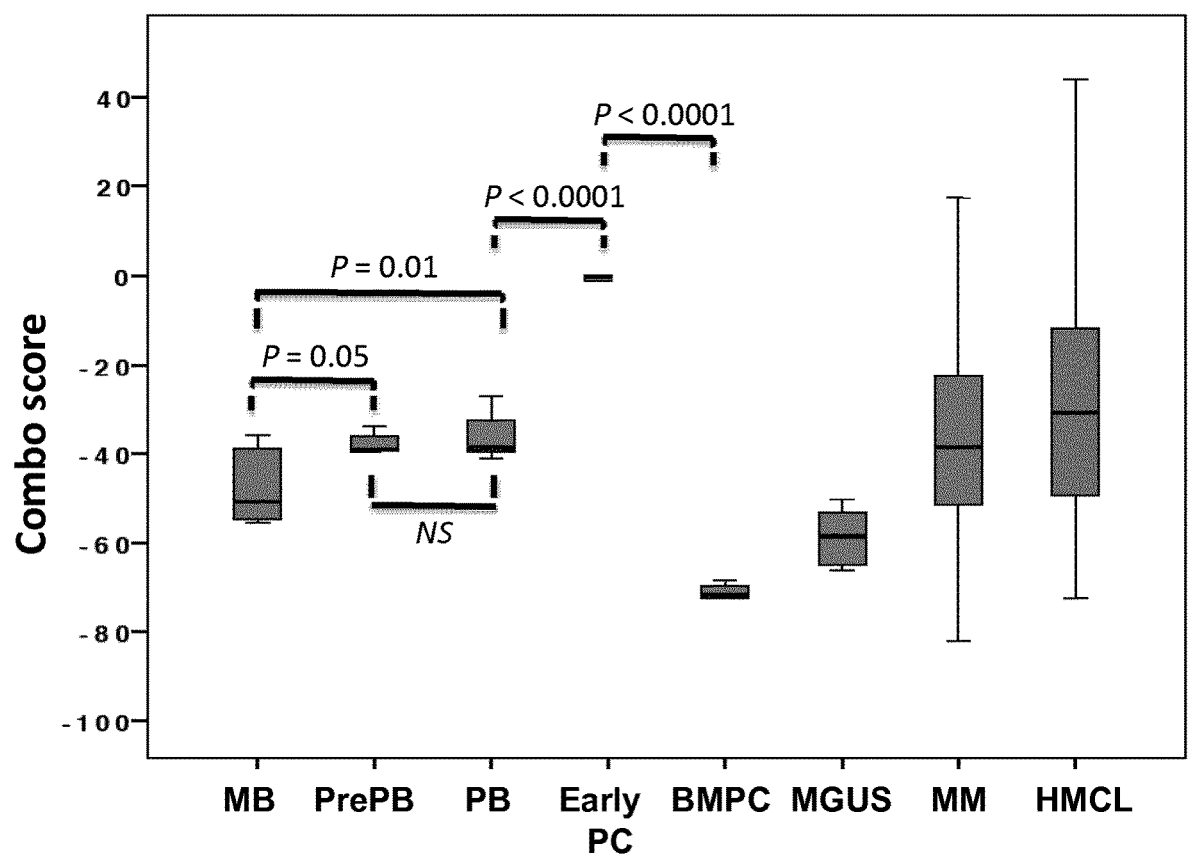

FIG. 5: HADMS score in normal plasma cell differentiation.

HADMS score in normal memory B cells (MB, n=5), normal preplasmablasts (PrePB, n=5), normal plasmablasts (PB, n=5), normal early plasma cells (Early PC, n=5), normal bone marrow plasma cells (n=7), in pre-malignant plasma cells of patients with monoclonal gammopathy of undetermined significance (MGUS, n=5), in multiple myeloma cells of patients with intramedullary MM (n=206) and in human myeloma cell lines (n=40).

Figure 6:
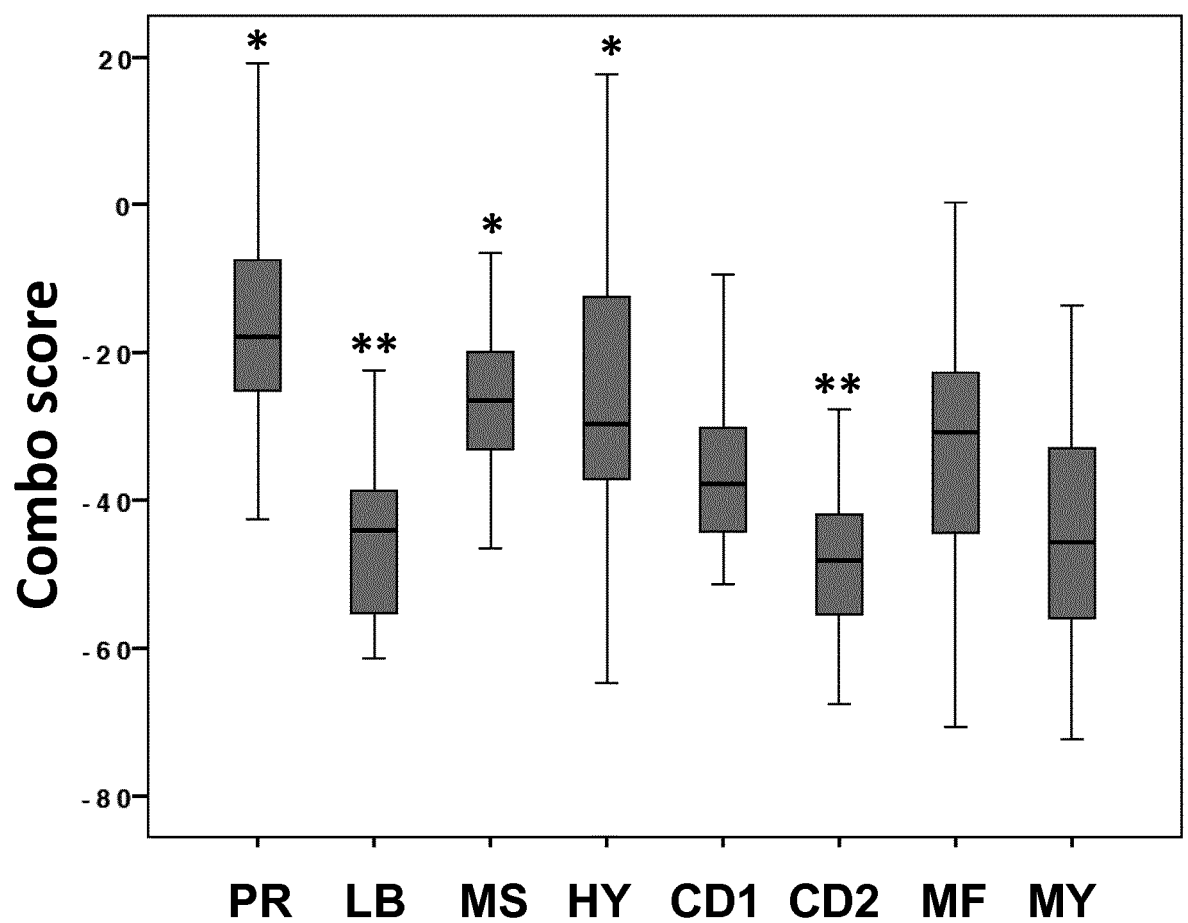

FIG. 6: HADMS in MMCs of patients using UAMS-TT2 cohort.

The HADMS score was computed for MMCs of patients belonging to the 8 groups of the UAMS molecular classification of multiple myeloma, using UAMS-TT2 cohort. PR: proliferation, LB: low bone disease, MS: MMSET, HY: hyperdiploid, CD1: Cyclin D1, CD2: Cyclin D2, MF: MAF, MY: myeloid. * Indicate that the score value is significantly higher in the group compared to all the patients of the cohort (P<0.05). ** Indicate that the score value is significantly lower in the group compared to all the patients of the cohort (P<0.05).

EXAMPLE

Material & Methods

Human Myeloma Cell Lines (HMCLs) and Primary Multiple Myeloma Cells of Patients.

Human myeloma cell lines HMCLs, N=40 were obtained as previously described (Gu, 2000; Moreaux, 2011; Rebouissou, 1998; Tarte, 1999; Zhang, 1994) or purchased from DSMZ and American Type Culture Collection. Microarray data are deposited in the ArrayExpress public database (accession numbers E-TABM-937 and E-TABM-1088). Patients presenting with previously untreated multiple myeloma (N=206) or monoclonal gammopathy of undetermined significance (N=5) at the university hospitals of Heidelberg and Montpellier as well as 7 healthy donors have been included in the study approved by the ethics committee of Montpellier and Heidelberg after written informed consent in accordance with the Declaration of Helsinki. Clinical parameters and treatment regimens of the MM patients included in the Heidelberg-Montpellier (HM) cohort were previously described (Hose, 2011). Gene expression profiling (GEP) of purified MMCs was assayed using Affymetrix U133 2.0 plus microarrays (Affymetrix, Santa Clara, Calif., USA) as described (De Vos, 2002) and data normalized using the MAS5 Affymetrix algorithm. The .CEL and MAS5 files are deposited in the ArrayExpress public database (http://www.ebi.ac.uk/arrayexpress/), under accession number E-MTAB-362. We also used publicly available MAS5 normalized GEP data (GEO, http://www.ncbi.nlm.nih.gov/geo/, accession number GSE2658) from purified MMCs of a cohort of 345 patients treated with total therapy 2 protocol (UAMS-TT2 cohort) at the University of Arkansas for Medical Sciences (UAMS, Little Rock, USA) (Barlogie, 2006). T(4; 14) translocation was evaluated using MMSET spike expression (Kassambara, 2012) and del17p13 surrogated by TP53 probe set signal (Xiong, 2008) for UAMS-TT2 patients. Gene expression data of normal memory B cells (MB), preplasmasts, plasmablasts and early plasma cells (Jourdan, 2009; Jourdan, 2011) are deposited in the ArrayExpress databases under accession numbers E-MEXP-2360 and E-MEXP-3034.

Identification of Genes Deregulated by HDACi+DNMTi Combination.

5 HMCLs (XG-5, XG-6, XG-7, XG-20 and LP1) were treated with 0.5 μmol/L Decitabine (Sigma, St Louis, Mo.) for 7 days in RPMI 1640, 10% fetal bovine serum supplemented with IL-6 for IL-6 dependent HMCLs. During the last 24 hours, 0.33 μmol/L TSA (Sigma) was added as described by Heller et at (Heller, 2008). Whole genome gene expression profiling was assayed with Affymetrix U133 2.0 plus microarrays (Affymetrix).

Sensitivity of Primary Myeloma Cells to HDACi+DNMTi Combination.

Primary myeloma cells of 10 patients were cultured with or without graded concentrations of Decitabine and TSA. Primary myeloma cells of 12 patients were cultured with or without graded concentrations of 5-azacitidine (Sigma) and vorinostat (SAHA) (Sigma). MMCs cytotoxicity was evaluated using anti-CD138-PE mAb (Immunotech, Marseille, France) as described (Mahtouk, 2004; Moreaux, 2012). Results were analyzed using GraphPad Prism (http://www.graphpad.com/scientific-software/prism/).

Statistical Analysis

Gene expression data were analyzed using SAM (Significance Analysis of Microarrays) software (Cui, 2003) as published (Kassambara, 2012). The statistical significance of differences in overall survival between groups of patients was calculated by the log-rank test. Multivariate analysis was performed using the Cox proportional hazards model. Survival curves were plotted using the Kaplan-Meier method. All these analyses have been done with R.2.10.1 (http://www.r-project.org/) and bioconductor version 2.5. Histone acetylation/DNA methylation risk score (termed HADMS Score) was built using our previously published methodology with the Decitabine/TSA combination deregulated prognostic genes (Moreaux, 2012; Moreaux, 2013). Briefly, HADMS Score was constructed as the sum of the Cox model beta coefficients of each of the Decitabine/TSA combination deregulated genes with a prognostic value, weighted by ±1 according to the patient MMC signal above or below the probeset maxstat value (Kassambara, 2012; Moreaux, 2012; Moreaux, 2013). Significantly enriched pathways were identified using Reactome functional interaction map. Gene set enrichment analysis was carried out by computing overlaps with canonical pathways and gene ontology gene sets obtained from the Broad Institute (Subramanian, 2005).

Results

Identification of Genes whose Expression is Deregulated by Decitabine and Trichostatin a Combination and Associated with a Prognostic Value in Multiple Myeloma.

Using gene expression microarrays, the inventors analyzed gene expression changes in 5 HMCLs after sublethal (Table 1) treatment of decitabine and TSA combination (Heller, 2008). Decitabine and TSA treatment resulted in a significant upregulation of 375 genes (SAM supervised paired analysis, FDR<5%; Table 2). REACTOME analysis revealed that decitabine/TSA-regulated genes are significantly enriched in genes related to interferon signaling (P<0.0001; FDR=1E-3), cell adhesion molecules (P<0.0001; FDR=1.6E-4), antigen processing and presentation (P<0.0001; FDR=7.6E-5) and EGF receptor signaling (P=0.0004; FDR=4.3E-3) pathways (Table 3). In order to identify genes deregulated by HDAC and DNMT linked with important function in MM pathophysiology, the inventors researched the genes deregulated by decitabine and TSA treatment whose expression is associated with a prognostic value using Maxstat R function and Benjamini-Hochberg multiple testing correction (Kassambara, 2012). Among the 375 genes, 42 genes had a bad prognostic value and 54 a good one in our cohort of 206 newly-diagnosed patients (HM cohort) (Table A). The prognostic information of decitabine and TSA combination regulated genes was gathered in a HADMS score as described in Materials and Methods section (FIG. 1). HADMS score values in normal, premalignant or malignant plasma cells are displayed in FIG. 2. HADMS score value was significantly higher in MMC from MGUS patients compared to normal BMPCs (P=0.009; FIG. 2). MMCs of patients have a significantly higher HADMS score than plasma cells from MGUS-patients (P=0.003) and HMCLs the highest score (P<0.001) (FIG. 2). Investigating the HADMS score in the 8 groups of the molecular classification of multiple myeloma, HADMS score was significantly higher in the proliferation, t(4; 14) and hyperdiploid subgroups (P<0.001; P=0.001 and P<0.001 respectively) and significantly lower in the low bone disease and CD2 subgroups (P=0.002 and P<0.001) (Zhan, 2006) (FIG. 6).

TABLE 1

Cell viability of HMCLs treated with 0.5 μM decitabine for 7 days and 0.33 μM during the last 24 hours. Data are the mean percentages ± SD of viable cells evaluated by trypan blue exclusion (3 experiments).

| | | Cell viability (%) | | | |
|---|---|---|---|---|---|
| | | | | Day 7 | |
| | | Day 3 | | | 5-aza and TSA during |
| HMCLS | Day 0 | Control | 5-aza | Control | the last 24 h |
| XG-5 | 70 ± 2 | 70 ± 1 | 65 ± 5 | 81 ± 5 | 69 ± 7 |
| XG-6 | 90 ± 2 | 90 ± 2 | 90 ± 1 | 93 ± 5 | 79 ± 2 |

TABLE 1-continued

Cell viability of HMCLs treated with 0.5 µM decitabine for 7 days and 0.33 µM during the last 24 hours. Data are the mean percentages ± SD of viable cells evaluated by trypan blue exclusion (3 experiments).

| | Cell viability (%) | | | | |
|---|---|---|---|---|---|
| | | Day 3 | | Day 7 | |
| HMCLS | Day 0 | Control | 5-aza | Control | 5-aza and TSA during the last 24 h |
| XG-7 | 100 ± 0 | 90 ± 2 | 90 ± 2 | 92 ± 4 | 83 ± 6 |
| XG-20 | 100 ± 0 | 91 ± 3 | 91 ± 3 | 95 ± 5 | 80 ± 5 |
| LP1 | 100 ± 0 | 91 ± 2 | 91 ± 2 | 94 ± 5 | 87 ± 3 |

TABLE 2

Genes overexpressed in decitabine/TSA treated HMCLs. Five HMCLs were cultured with or without 0.5 µM decitabine for 7 days and with or without 0.33 µM TSA for the last 24 hours. Gene expression was profiled with Affymetrix U133 plus 2.0 microarray. Genes significantly differentially expressed between control and decitabine + TSA treated cells were identified using SAM supervised paired analysis with a 5% false discovery rate.

| Probeset | Gene | Ratio | Banding |
|---|---|---|---|
| Intercellular communication and membrane proteins | | | |
| 205997_at | ADAM28 | 27.0 | 8p21.2 |
| 201952_at | ALCAM | 16.4 | 3q13.1 |
| 209462_at | APLP1 | 24.5 | 19q13.1 |
| 211404_s_at | APLP2 | 2.5 | 11q23-q25\|11q24 |
| 205239_at | AREG | 24.1 | 4q13-q21 |
| 217767_at | C3 | 10.1 | 19p13.3-p13.2 |
| 209906_at | C3AR1 | 17.9 | 12p13.31 |
| 204103_at | CCL4 | 3.7 | 17q12 |
| 226545_at | CD109 | 6.3 | 6q13 |
| 216379_x_at | CD24 | 15.5 | 6q21 |
| 229221_at | CD44 | 3.2 | 11p13 |
| 213958_at | CD6 | 8.8 | 11q13 |
| 203904_x_at | CD82 | 3.2 | 11p11.2 |
| 204440_at | CD83 | 3.8 | 6p23 |
| 201005_at | CD9 | 15.2 | 12p13.3 |
| 201131_s_at | CDH1 | 107.5 | 16q22.1 |
| 213800_at | CFH | 7.9 | 1q32 |
| 221698_s_at | CLEC7A | 9.5 | 12p13.2-p12.3 |
| 1556499_s_at | COL1A1 | 11.6 | 17q21.3-q22.1 |
| 202403_s_at | COL1A2 | 5.4 | 7q22.1 |
| 205898_at | CX3CR1 | 5.2 | 3p21\|3p21.3 |
| 208779_x_at | DDR1 | 2.7 | 6p21.3 |
| 226281_at | DNER | 15.3 | 2q36.3 |
| 202668_at | EFNB2 | 5.2 | 13q33 |
| 225078_at | EMP2 | 7.4 | 16p13.2 |
| 213506_at | F2RL1 | 158.2 | 5q13 |
| 201579_at | FAT | 14.1 | 4q35 |
| 212464_s_at | FN1 | 79.4 | 2q34 |
| 204222_s_at | GLIPR1 | 3.2 | 12q21.1 |
| 231166_at | GPR155 | 4.2 | 2q31.1 |
| 229055_at | GPR68 | 5.8 | 14q31 |
| 200696_s_at | GSN | 7.6 | 9q33 |
| 217478_s_at | HLA-DMA | 2.6 | 6p21.3 |
| 203932_at | HLA-DMB | 4.2 | 6p21.3 |
| 211990_at | HLA-DPA1 | 7.6 | 6p21.3 |
| 201137_s_at | HLA-DPB1 | 5.5 | 6p21.3 |
| 212671_s_at | HLA-DQA1 | 6.5 | 6p21.3 |
| 212998_x_at | HLA-DQB1 | 18.5 | 6p21.3 |
| 208894_at | HLA-DRA | 7.9 | 6p21.3 |
| 215193_x_at | HLA-DRB1 | 4.1 | 6p21.3 |
| 208306_x_at | HLA-DRB5 | 3.6 | 6p21.3 |
| 217362_x_at | HLA-DRB6 | 4.4 | 6p21.3 |
| 219403_s_at | HPSE | 5.6 | 4q21.3 |
| 210095_s_at | IGFBP3 | 5.3 | 7p13-p12 |
| 206172_at | IL13RA2 | 32.9 | Xq13.1-q28 |

TABLE 2-continued

Genes overexpressed in decitabine/TSA treated HMCLs. Five HMCLs were cultured with or without 0.5 µM decitabine for 7 days and with or without 0.33 µM TSA for the last 24 hours. Gene expression was profiled with Affymetrix U133 plus 2.0 microarray. Genes significantly differentially expressed between control and decitabine + TSA treated cells were identified using SAM supervised paired analysis with a 5% false discovery rate.

| Probeset | Gene | Ratio | Banding |
|---|---|---|---|
| 203233_at | IL4R | 3.5 | 16p11.2-12.1 |
| 216331_at | ITGA7 | 5.5 | 12q13 |
| 207509_s_at | LAIR2 | 4.9 | 19q13.4 |
| 205569_at | LAMP3 | 16.4 | 3q26.3-q27 |
| 221581_s_at | LAT2 | 4.3 | 7q11.23 |
| 200923_at | LGALS3BP | 18.2 | 17q25 |
| 208933_s_at | LGALS8 | 14.0 | 1q42-q43 |
| 225060_at | LRP11 | 40.4 | 6q25.1 |
| 235568_at | MCEMP1 | 12.3 | 19p13.2 |
| 210605_s_at | MFGE8 | 4.5 | 15q25 |
| 212473_s_at | MICAL2 | 11.3 | 11p15.3 |
| 205959_at | MMP13 | 221.2 | 11q22.3 |
| 212509_s_at | MXRA7 | 15.0 | 17q25.1 |
| 203413_at | NELL2 | 6.2 | 12q13.11-q13.12 |
| 204105_s_at | NRCAM | 3.2 | 7q31.1-q31.2 |
| 214617_at | PRF1 | 36.7 | 10q22 |
| 212646_at | RAFTLIN | 3.3 | 3p25.1-p24.3 |
| 212158_at | SDC2 | 26.3 | 8q22-q23 |
| 202071_at | SDC4 | 5.3 | 20q12 |
| 204563_at | SELL | 4.1 | 1q23-q25 |
| 201427_s_at | SEPP1 | 104.7 | 5q31 |
| 228726_at | SERPINB1 | 6.1 | 6p25 |
| 211474_s_at | SERPINB6 | 8.2 | 6p25 |
| 209723_at | SERPINB9 | 33.2 | 6p25 |
| 202283_at | SERPINF1 | 51.0 | 17p13.1 |
| 205352_at | SERPINI1 | 8.4 | 3q26.1 |
| 209848_s_at | SILV | 12.6 | 12q13-q14 |
| 206310_at | SPINK2 | 22.3 | 4q12 |
| 205016_at | TGFA | 6.0 | 2p13 |
| 226625_at | TGFBR3 | 3.9 | 1p33-p32 |
| 202085_at | TJP2 | 4.7 | 9q13-q21 |
| 218113_at | TMEM2 | 3.0 | 9q13-q21 |
| 202688_at | TNFSF10 | 9.9 | 3q26 |
| 207426_s_at | TNFSF4 | 3.4 | 1q25 |
| 206907_at | TNFSF9 | 7.2 | 19p13.3 |
| 203476_at | TPBG | 8.1 | 6q14-q15 |
| 200931_s_at | VCL | 3.4 | 10q22.1-q23 |
| 227530_at | AKAP12 | 29.7 | 6q24-q25 |
| Signal transduction | | | |
| 218501_at | ARHGEF3 | 5.6 | 3p21-p13 |
| 227915_at | ASB2 | 4.6 | 14q31-q32 |
| 209682_at | CBLB | 2.4 | 3q13.11 |
| 213385_at | CHN2 | 2.7 | 7p15.3 |
| 201041_s_at | DUSP1 | 3.6 | 5q34 |
| 221563_at | DUSP10 | 2.1 | 1q41 |
| 207111_at | EMR1 | 10.9 | 19p13.3 |
| 202609_at | EPS8 | 3.6 | 12q13 |
| 224657_at | ERRFI1 | 2.5 | 1p36.12-36.33 |
| 226269_at | GDAP1 | 3.6 | 8q21.11 |
| 204472_at | GEM | 5.3 | 8q13-q21 |
| 227692_at | GNAI1 | 4.0 | 7q21 |
| 214022_s_at | IFITM1 | 5.9 | 11p15.5 |
| 205227_at | IL1RAP | 5.1 | 3q28 |
| 231779_at | IRAK2 | 3.6 | 3p25.3 |
| 235252_at | KSR | 3.3 | 17q11.2 |
| 202086_at | MX1 | 8.5 | 21q22.3 |
| 223218_s_at | NFKBIZ | 6.1 | 3p12-q12 |
| 203964_at | NMI | 3.6 | 2p24.3-q21.3 |
| 225626_at | PAG1 | 13.8 | 8q21.13 |
| 203879_at | PIK3CD | 4.5 | 1p36.2 |
| 201939_at | PLK2 | 5.2 | 5q12.1-q13.2 |
| 203680_at | PRKAR2B | 3.9 | 7q22 |
| 203355_s_at | PSD3 | 2.9 | 8pter-p23.3 |
| 202252_at | RAB13 | 22.7 | 1q21.2 |
| 219622_at | RAB20 | 7.7 | 13q34 |
| 217764_s_at | RAB31 | 5.9 | 18p11.3 |
| 217762_s_at | RAB31 | 2.9 | 18p11.3 |
| 212561_at | RAB6IP1 | 5.1 | 11p15.4 |
| 1553185_at | RASEF | 2.9 | 9q21.32 |

TABLE 2-continued

Genes overexpressed in decitabine/TSA treated HMCLs. Five HMCLs were cultured with or without 0.5 µM decitabine for 7 days and with or without 0.33 µM TSA for the last 24 hours. Gene expression was profiled with Affymetrix U133 plus 2.0 microarray. Genes significantly differentially expressed between control and decitabine + TSA treated cells were identified using SAM supervised paired analysis with a 5% false discovery rate.

| Probeset | Gene | Ratio | Banding |
|---|---|---|---|
| 230233_at | RASGEF1B | 3.4 | 4q21.3 |
| 225946_at | RASSF8 | 3.3 | 12p12.3 |
| 203485_at | RTN1 | 8.0 | 14q23.1 |
| 34408_at | RTN2 | 5.1 | 19q13.32 |
| 226549_at | SBK1 | 3.8 | 16p11.2 |
| 209969_s_at | STAT1 | 6.3 | 2q32.2 |
| 206118_at | STAT4 | 8.3 | 2q32.2-q32.3 |
| 202695_s_at | STK17A | 3.2 | 7p12-p14 |
| 220260_at | TBC1D19 | 4.1 | 4p15.2 |
| 213107_at | TNIK | 4.9 | 3q26.2 |
| Cytoskeleton | | | |
| 224694_at | ANTXR1 | 4.3 | 2p13.1 |
| 225524_at | ANTXR2 | 6.4 | 4q21.21 |
| 212077_at | CALD1 | 24.8 | 7q33 |
| 212554_at | CAP2 | 6.8 | 6p22.3 |
| 224583_at | COTL1 | 3.2 | 16q24.1 |
| 212730_at | DMN | 3.6 | 15q26.3 |
| 225855_at | EPB41L5 | 3.4 | 2q14.2 |
| 217892_s_at | EPLIN | 2.7 | 12q13 |
| 208614_s_at | FLNB | 7.5 | 3p14.3 |
| 203854_at | IF | 3.8 | 4q25 |
| 226968_at | KIF1B | 2.6 | 1p36.2 |
| 203130_s_at | KIF5C | 7.1 | 2q23.1 |
| 201596_x_at | KRT18 | 2.3 | 12q13 |
| 225540_at | MAP2 | 23.1 | 2q34-q35 |
| 225407_at | MBP | 2.9 | 18q23 |
| 201976_s_at | MYO10 | 4.8 | 5p15.1-p14.3 |
| 203215_s_at | MYO6 | 13.7 | 6q13 |
| 218678_at | NES | 6.6 | 1q23.1 |
| 210986_s_at | TPM1 | 4.2 | 15q22.1 |
| 204141_at | TUBB2 | 6.3 | 6p25 |
| Cell cycle | | | |
| 221555_x_at | CDC14B | 3.9 | 9q22.33 |
| 225685_at | CDC42EP3 | 2.6 | 2p21 |
| 202284_s_at | CDKN1A | 2.9 | 6p21.2 |
| 213348_at | CDKN1C | 2.8 | 11p15.5 |
| 31874_at | GAS2L1 | 7.0 | 22q12.2 |
| 1553599_a_at | SYCP3 | 22.4 | 12q |
| Metabolism | | | |
| 209459_s_at | ABAT | 6.5 | 16p13.2 |
| 209993_at | ABCB1 | 12.2 | 7q21.1 |
| 209122_at | ADFP | 4.6 | 9p22.1 |
| 226325_at | ADSSL1 | 27.9 | 14q32.33 |
| 209160_at | AKR1C3 | 22.1 | 10p15-p14 |
| 201243_s_at | ATP1B1 | 6.4 | 1q24 |
| 213106_at | ATP8A1 | 2.7 | 4p14-p12 |
| 206633_at | CHRNA1 | 39.2 | 2q24-q32 |
| 213317_at | CLIC5 | 4.8 | 6p12.1-21.1 |
| 231265_at | COX7B2 | 54.1 | 4p12 |
| 201116_s_at | CPE | 13.1 | 4q32.3 |
| 202295_s_at | CTSH | 3.1 | 15q24-q25 |
| 210074_at | CTSL2 | 4.7 | 9q22.2 |
| 203475_at | CYP19A1 | 3.9 | 15q21.1 |
| 202436_s_at | CYP1B1 | 22.7 | 2p21 |
| 228391_at | CYP4V2 | 3.9 | 4q35.1-q35.2 |
| 214079_at | DHRS2 | 11.0 | 14q11.2 |
| 219532_at | ELOVL4 | 18.3 | 6q14 |
| 209392_at | ENPP2 | 76.3 | 8q24.1 |
| 202838_at | FUCA1 | 4.2 | 1p34 |
| 211458_s_at | GABARAPL1 | 25.4 | 12p13.2 |
| 231577_s_at | GBP1 | 10.0 | 1p22.2 |
| 202748_at | GBP2 | 3.2 | 1p22.2 |
| 223434_at | GBP3 | 18.2 | 1p22.2 |
| 213343_s_at | GDPD5 | 7.3 | 11q13.4-q13.5 |
| 226160_at | H6PD | 2.4 | 1p36 |
| 1552767_a_at | HS6ST2 | 8.9 | Xq26.2 |
| 205404_at | HSD11B1 | 16.8 | 1q32-q41 |
| 230966_at | IL4I1 | 4.4 | 19q13.3-q13.4 |
| 203710_at | ITPR1 | 3.4 | 3p26-p25 |
| 204179_at | MB | 25.5 | 22q13.1 |
| 204059_s_at | ME1 | 2.4 | 6q12 |
| 225782_at | MSRB3 | 3.3 | 12q14.3 |
| 214440_at | NAT1 | 2.5 | 8p23.1-p21.3 |
| 211685_s_at | NCALD | 2.5 | 8q22-q23 |
| 210519_s_at | NQO1 | 2.8 | 16q22.1 |
| 219369_s_at | OTUB2 | 2.6 | 14q32.13 |
| 202430_s_at | PLSCR1 | 5.4 | 3q23 |
| 204286_s_at | PMAIP1 | 3.8 | 18q21.32 |
| 206345_s_at | PON1 | 5.0 | 7q21.3 |
| 201876_at | PON2 | 2.9 | 7q21.3 |
| 202458_at | PRSS23 | 10.6 | 11q14.1 |
| 238017_at | RDHE2 | 48.7 | 8q12.1 |
| 204730_at | RIMS3 | 2.6 | 1pter-p22.2 |
| 217983_s_at | RNASET2 | 2.5 | 6q27 |
| 242625_at | RSAD2 | 56.7 | 2p25.2 |
| 210592_s_at | SAT | 6.4 | Xp22.1 |
| 210432_s_at | SCN3A | 3.6 | 2q24 |
| 223391_at | SGPP1 | 4.6 | 14q23.2 |
| 226728_at | SLC27A1 | 2.4 | 19p13.11 |
| 216236_s_at | SLC2A14 | 4.3 | 12p13.31 |
| 202497_x_at | SLC2A3 | 28.1 | 12p13.3 |
| 202219_at | SLC6A8 | 6.3 | Xq28 |
| 216370_s_at | TKTL1 | 56.6 | Xq28 |
| 223949_at | TMPRSS3 | 6.8 | 21q22.3 |
| 204140_at | TPST1 | 3.2 | 7q11.21 |
| 213423_x_at | TUSC3 | 13.7 | 8p22 |
| 219211_at | USP18 | 30.6 | 22q11.21 |
| Protein binding | | | |
| 206385_s_at | ANK3 | 14.7 | 10q21 |
| 208792_s_at | CLU | 3.3 | 8p21-p12 |
| 203695_s_at | DFNA5 | 9.2 | 7p15 |
| 200606_at | DSP | 2.5 | 6p24 |
| 200878_at | EPAS1 | 3.5 | 2p21-p16 |
| 225328_at | FBXO32 | 8.3 | 8q24.13 |
| 200799_at | HSPA1A | 63.1 | 6p21.3 |
| 211538_s_at | HSPA2 | 14.0 | 14q24.1 |
| 228153_at | IBRDC2 | 5.6 | 6p22.3 |
| 201315_x_at | IFITM2 | 4.9 | 11p15.5 |
| 209270_at | LAMB3 | 12.5 | 1q32 |
| 203186_s_at | S100A4 | 13.7 | 1q21 |
| 204030_s_at | SCHIP1 | 3.7 | 3q25.32-q25.33 |
| 33323_r_at | SFN | 4.7 | 1p36.11 |
| 218404_at | SNX10 | 3.6 | 7p15.2 |
| 205573_s_at | SNX7 | 24.1 | 1p21.3 |
| 209198_s_at | SYT11 | 9.7 | 1q21.2 |
| 232914_s_at | SYTL2 | 13.8 | 11q14 |
| 232692_at | TDRD6 | 9.2 | 6p12.3 |
| 213361_at | TDRD7 | 3.3 | 9q22.33 |
| 228285_at | TDRD9 | 14.7 | 14q32.33 |
| Cancer testis antigens | | | |
| 235700_at | CT45-2 | 30.9 | Xq26.3 |
| 214603_at | MAGEA2 | 30.6 | Xq28 |
| 210437_at | MAGEA9 | 5.4 | Xq28 |
| 204086_at | PRAME | 12.2 | 22q11.22 |
| 220922_s_at | SPANXA1 | 55.2 | Xq27.1 |
| 220217_s_at | SPANXC | 4.9 | Xq27.1 |
| 210394_x_at | SSX4 | 12.1 | Xp11.23 |
| 207281_x_at | VCX | 9.5 | Xp22 |
| Nuclear proteins and transcription factors | | | |
| 238825_at | ACRC | 9.2 | Xq13.1 |
| 202672_s_at | ATF3 | 3.4 | 1q32.3 |
| 219870_at | ATF7IP2 | 2.9 | 16p13.13 |
| 206588_at | DAZL | 138.5 | 3p24.3 |
| 222793_at | DDX58 | 9.7 | 9p12 |

TABLE 2-continued

Genes overexpressed in decitabine/TSA treated HMCLs. Five HMCLs were cultured with or without 0.5 μM decitabine for 7 days and with or without 0.33 μM TSA for the last 24 hours. Gene expression was profiled with Affymetrix U133 plus 2.0 microarray. Genes significantly differentially expressed between control and decitabine + TSA treated cells were identified using SAM supervised paired analysis with a 5% false discovery rate.

| Probeset | Gene | Ratio | Banding |
|---|---|---|---|
| 201694_s_at | EGR1 | 3.4 | 5q31.1 |
| 205249_at | EGR2 | 14.8 | 10q21.1 |
| 225645_at | EHF | 8.1 | 11p12 |
| 228260_at | ELAVL2 | 4.0 | 9p21 |
| 210827_s_at | ELF3 | 3.7 | 1q32.2 |
| 203349_s_at | ETV5 | 4.7 | 3q28 |
| 209603_at | GATA3 | 5.2 | 10p15 |
| 208886_at | H1F0 | 3.4 | 22q13.1 |
| 214469_at | HIST1H2AE | 9.0 | 6p22.2-p21.1 |
| 235456_at | HIST1H2BD | 7.6 | 6p21.3 |
| 210387_at | HIST1H2BG | 6.7 | 6p21.3 |
| 211597_s_at | HOP | 13.8 | 4q11-q12 |
| 208937_s_at | ID1 | 4.2 | 20q11 |
| 207826_s_at | ID3 | 44.6 | 1p36.13-p36.12 |
| 219209_at | IFIH1 | 4.1 | 2p24.3-q24.3 |
| 202597_at | IRF6 | 7.3 | 1q32.3-q41 |
| 208436_s_at | IRF7 | 7.6 | 11p15.5 |
| 225798_at | JAZF1 | 2.7 | 7p15.2-p15.1 |
| 1555420_a_at | KLF7 | 2.7 | 2q32 |
| 236565_at | LARP6 | 5.2 | 15q23 |
| 221011_s_at | LBH | 6.7 | 2p23.1 |
| 229475_at | MAEL | 51.3 | 1q24.1 |
| 235457_at | MAML2 | 4.2 | 11q21 |
| 242794_at | MAML3 | 6.9 | 4q28 |
| 238430_x_at | MGC19764 | 3.2 | 17q12 |
| 224917_at | MIRN21 | 6.3 | — |
| 226066_at | MITF | 2.4 | 3p14.2-p14.1 |
| 223484_at | NMES1 | 204.9 | 15q21.1 |
| 205552_s_at | OAS1 | 6.9 | 12q24.1 |
| 204972_at | OAS2 | 3.2 | 12q24.2 |
| 210797_s_at | OASL | 3.8 | 12q24.2 |
| 218543_s_at | PARP12 | 9.4 | 7q34 |
| 224701_at | PARP14 | 10.5 | 3q21.1 |
| 223220_s_at | PARP9 | 12.5 | 3q13-q21 |
| 204082_at | PBX3 | 2.1 | 9q33-q34 |
| 209598_at | PNMA2 | 4.2 | 8p21.2 |
| 212636_at | QKI | 3.1 | 6q26-27 |
| 223394_at | SERTAD1 | 3.4 | 19q13.1-q13.2 |
| 225123_at | SESN3 | 10.7 | 11q21 |
| 201416_at | SOX4 | 6.4 | 6p22.3 |
| 209762_x_at | SP110 | 5.6 | 2q37.1 |
| 209306_s_at | SWAP70 | 3.0 | 11p15 |
| 227279_at | TCEAL3 | 2.6 | Xq22.2 |
| 212761_at | TCF7L2 | 4.5 | 10q25.3 |
| 203313_s_at | TGIF | 4.4 | 18p11.3 |
| 228988_at | ZNF6 | 3.5 | Xq21.1-q21.2 |
| Apoptosis | | | |
| 201012_at | ANXA1 | 10.9 | 9q12-q21.2\|9q12-q21.2 |
| 210538_s_at | BIRC3 | 7.9 | 11q22 |
| 210026_s_at | CARD10 | 7.2 | 22q13.1 |
| 205483_s_at | G1P2 | 11.9 | 1p36.33 |
| 204415_at | G1P3 | 10.4 | 1p35 |
| 201631_s_at | IER3 | 4.4 | 6p21.3 |
| 202411_at | IFI27 | 9.3 | 14q32 |
| 221690_s_at | NALP2 | 20.4 | 19q13.42 |
| 237461_at | NALP7 | 7.2 | 19q13.42 |
| 228617_at | XAF1 | 26.2 | 17p13.1 |
| Others | | | |
| 1559336_at | — | 18.4 | — |
| 211781_x_at | — | 7.5 | — |
| 222184_at | — | 3.1 | — |
| 225842_at | — | 27.9 | — |
| 226725_at | — | 6.1 | — |
| 227193_at | — | 4.1 | — |
| 227290_at | — | 2.8 | — |
| 227503_at | — | 5.8 | — |
| 229968_at | — | 17.0 | — |
| 230383_x_at | — | 5.9 | — |
| 230499_at | — | 3.7 | — |
| 230860_at | — | 2.9 | — |
| 234250_at | — | 5.1 | — |
| 235072_s_at | — | 8.1 | — |
| 235276_at | — | 18.0 | — |
| 236856_x_at | — | 2.3 | — |
| 238725_at | — | 2.6 | — |
| 240979_at | — | 4.4 | — |
| 241262_at | — | 2.3 | — |
| 241763_s_at | — | 7.2 | — |
| 241898_at | — | 2.7 | — |
| 212543_at | AIM1 | 11.3 | 6q21 |
| 203404_at | ARMCX2 | 17.9 | Xq21.33-q22.2 |
| 225283_at | ARRDC4 | 4.7 | 15q26.3 |
| 212599_at | AUTS2 | 3.8 | 7q11.22 |
| 215440_s_at | BEXL1 | 10.2 | Xq22.1-q22.3 |
| 212560_at | C11orf32 | 7.7 | — |
| 221260_s_at | C12orf22 | 2.9 | 12q13.11-q13.12 |
| 1559584_a_at | C16orf54 | 29.9 | 16p11.2 |
| 230000_at | C17orf27 | 2.6 | 17q25.3 |
| 229973_at | C1orf173 | 16.8 | 1p31.1 |
| 210785_s_at | C1orf38 | 2.8 | 1p35.3 |
| 238480_at | chromosome 18 open reading frame 50 | 5.5 | — |
| 207030_s_at | CSRP2 | 7.9 | 12q21.1 |
| 219313_at | DKFZp434C0328 | 7.9 | 3q13.31 |
| 226000_at | DKFZp547A023 | 8.3 | 1p13.2 |
| 224952_at | DKFZP564D166 | 2.9 | 17q23.3 |
| 225355_at | DKFZP761M1511 | 9.6 | 5q35.2 |
| 235085_at | DKFZp761P0423 | 5.7 | 8p23.1 |
| 203498_at | DSCR1L1 | 4.3 | 6p21.1-p12.3 |
| 235759_at | EFCBP1 | 4.2 | 8q21.3 |
| 227609_at | EPSTI1 | 6.9 | 13q13.3 |
| 227410_at | FAM43A | 3.5 | 3q29 |
| 228745_at | FLJ13611 | 3.6 | 5q12.3 |
| 218986_s_at | FLJ20035 | 30.1 | 4q32.3 |
| 228423_at | FLJ21159 | 6.2 | 4q32.1 |
| 228152_s_at | FLJ31033 | 58.4 | 4q32.3 |
| 230012_at | FLJ34790 | 7.0 | 17p13.1 |
| 228937_at | FLJ38725 | 4.9 | 13q14.11 |
| 229559_at | FLJ40125 | 3.8 | 19q13.32 |
| 214453_s_at | IFI44 | 46.8 | 1p31.1 |
| 203153_at | IFIT1 | 66.9 | 10q25-q26 |
| 226757_at | IFIT2 | 13.9 | 10q23-q25 |
| 229450_at | IFIT3 | 21.2 | 10q24 |
| 203595_s_at | IFIT5 | 85.3 | 10q23.31 |
| 235048_at | KIAA0888 | 3.7 | 5q13.3 |
| 200897_s_at | KIAA0992 | 7.1 | 4q32.3 |
| 212906_at | KIAA1201 | 5.6 | 11q24.1 |
| 225525_at | KIAA1671 | 2.5 | — |
| 226702_at | LOC129607 | 26.4 | 2p25.2 |
| 241353_s_at | LOC202775 | 4.2 | 7q34 |
| 239624_at | LOC440885 | 27.2 | 2p11.1 |
| 224480_s_at | MGC11324 | 4.2 | 4q21.23 |
| 214696_at | MGC14376 | 2.8 | 17p13.3 |
| 227038_at | MGC26963 | 4.9 | 4q25 |
| 226395_at | MGC4677 | 19.7 | 2p11.2 |
| 207738_s_at | NCKAP1 | 3.3 | 2q32 |
| 229963_at | NGFRAP1L1 | 20.1 | Xq22.1 |
| 205380_at | PDZK1 | 9.3 | 1q21 |
| 212094_at | PEG10 | 23.9 | 7q21 |
| 217996_at | PHLDA1 | 8.6 | 12q15 |
| 225688_s_at | PHLDB2 | 8.7 | 3q13.2 |
| 231131_at | RP1-32F7.2 | 49.9 | Xq21.33 |
| 220167_at | TP53TG3 | 3.3 | 16p13 |
| 213293_s_at | TRIM22 | 11.9 | 11p15 |
| 227174_at | WDR72 | 7.0 | 15q21.3 |
| 224894_at | YAP1 | 3.7 | 11q13 |
| 219062_s_at | ZCCHC2 | 4.7 | 18q21.33 |

TABLE 3

REACTOME analysis revealed that decitabine/TSA-regulated genes are significantly enriched in genes related to interferon signaling (P < 0.0001; FDR = 1E−3), cell adhesion molecules (P < 0.0001; FDR = 1.6E−4), antigen processing and presentation (P < 0.0001; FDR = 7.6E−5) and EGF receptor signaling (P = 0.0004; FDR = 4.3E−3) pathways.

| Gene Set | Ratio of protein in gene set | Number of protein in gene set | Protein from network | P value | FDR | Nodes |
|---|---|---|---|---|---|---|
| Interferon Signaling | 0.0174 | 161 | 26 | 0 | <1.00e−03 | CD44, MX1, HLA-DQA1, HLA-DPA1, GBP2, GBP1, HLA-DRA, IFITM1, HLA-DRB1, IFITM2, OAS1, OAS2, HLA-DRB5, HLA-DPB1, DDX58, IFI27, OASL, USP18, EGR1, FLNB, HLA-DQB1, STAT1, IFIT3, IFIT2, IFIT1, IRF7 |
| Cell adhesion molecules (CAMs) | 0.0144 | 133 | 15 | 0 | <1.67e−04 | NRCAM, HLA-DQA1, HLA-DPA1, HLA-DRA, HLA-DRB1, ALCAM, HLA-DRB5, HLA-DPB1, HLA-DMB, SDC4, HLA-DMA, SDC2, HLA-DQB1, CDH1, CD6 |
| Antigen processing and presentation | 0.0082 | 76 | 11 | 0 | <7.69e−05 | HLA-DQA1, HLA-DPA1, HLA-DRA, HLA-DRB1, HSPA1A, HLA-DRB5, HLA-DPB1, HLA-DMB, HLA-DMA, HLA-DQB1, HSPA2 |
| EGF receptor signaling pathway | 0.0089 | 82 | 6 | 0.0004 | 4.44e−03 | PIK3CD, CBLB, AREG, TGFA, STAT4, STAT1 |

Evaluation of the Prognostic Significance of HADMS Score in Two Independent Cohorts of Patients.

Figure 3A:
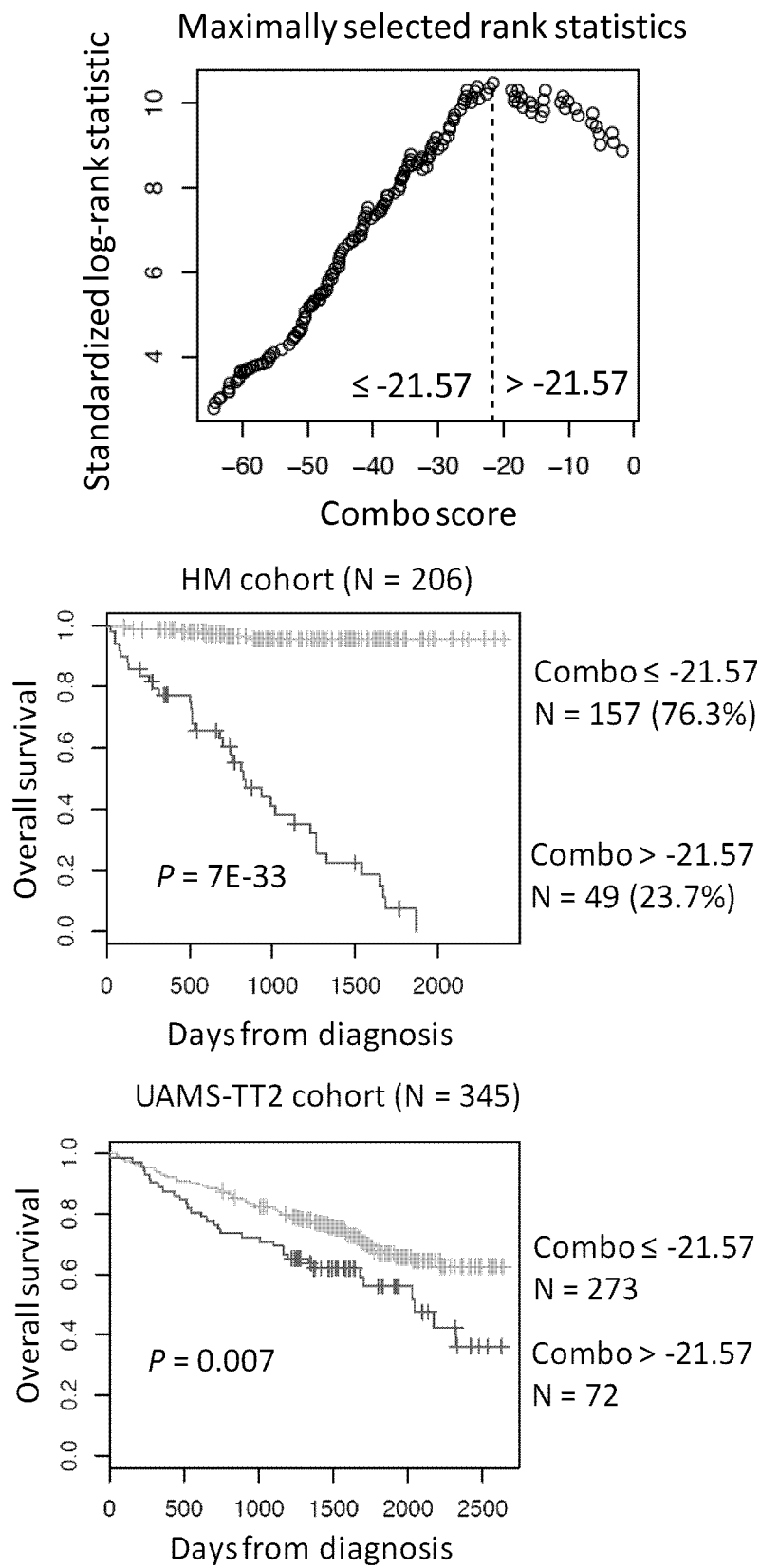
Figure 3B:
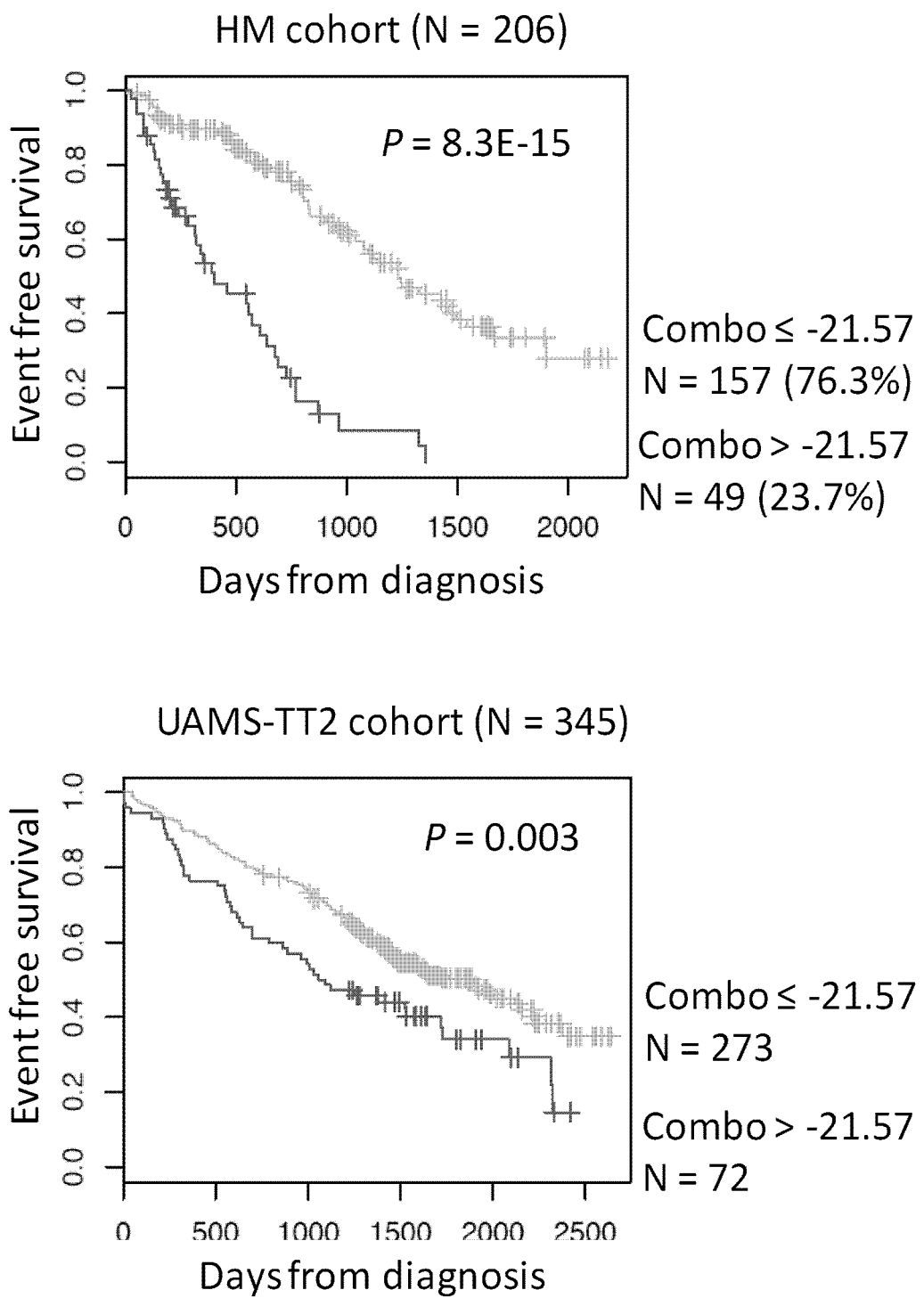

Using maxstat analysis for overall survival, HADMS score was significantly associated with high-risk myeloma in the 2 independent patients' cohorts, HM and UAMS-TT2 (FIG. 3A). Maxstat statistic test split the HM-patient cohort within 2 groups: a high-risk group of 23.7% patients (HADMS score>−21.57) with a 27 months median OS and a low risk group of 76.3% patients (HADMS score≤−21.57) with not reached median survival (P=7E−33; FIG. 3A). In the UAMS-TT2 cohort, a HADMSs score>−21.57 is associated with a high risk (P=0.007; FIG. 3A) in 20.8% of the patients. The HADMS score could also predict for event free survival (EFS). The high-risk group had a median EFS of 13 and 34 months in HM and UAMS-TT2 cohorts respectively and the low-risk group had a median EFS of 40 and 62 months (P=8.3E−15 and 0.003 respectively; FIG. 3B).

The prognostic value of the HADMS score was compared to usual prognostic factors (β2M, ISS, t(4; 14) and del17p) and published GEP-based risk scores: UAMS-HRS (Shaughnessy, 2007), IFM score (Decaux, 2008), GPI (Hose, 2011), RS score (Reme, 2013), DM score (Moreaux, 2012) and HA score (Moreaux, 2013). In univariate COX analysis, all of these factors had prognostic value (Table 4). Compared two by two or all together in multivariate COX analysis, HADMS score and β2M remained independent in the HM cohort. In UAMS-TT2 cohort, when compared two by two, HADMS score tested with IFM score, t(4; 14), del17p, GPI and DM score remained independent prognostic factors. When tested all together, UAMS-HRS, t(4; 14), del17p and HA score remained independent (Table 4).

TABLE 4

Cox univariate and multivariate analysis of OS in HM and TT2 patients' cohorts.

| | | HM Cohort OAS | | TT2 Cohort OAS | |
|---|---|---|---|---|---|
| | Pronostic variable | Proportional hazard ratio | P-value | Proportional hazard ratio | P-value |
| Univariate COX analysis - Overall survival | HADMS Score | 31.87 | <0.0001 | 1.73 | 0.008 |
| | β2m | 1.1 | <0.0001 | NA | NA |
| | ISS | 1.84 | 0.002 | NA | NA |
| | HRS | 2.37 | 0.01 | 4.67 | <0.0001 |
| | IFM score | 2.49 | 0.01 | 1.78 | 0.004 |
| | t(4; 14) | 3.32 | <0.0001 | 2.21 | 0.001 |
| | del17p | 3.44 | 0.02 | 2.46 | <0.0001 |
| | GPI | 2.54 | <0.0001 | 1.75 | <0.0001 |
| | RS | 4.16 | <0.0001 | 1.91 | <0.0001 |
| | DM Score | 6.02 | <0.0001 | 1.89 | 0.001 |
| | HA Score | 7.43 | <0.0001 | 1.96 | <0.0001 |
| Multivariate COX analysis - Overall survival | HADMS Score | 29.21 | <0.0001 | NA | NA |
| | ISS | 1.42 | NS | NA | NA |
| | HADMS Score | 35.72 | <0.0001 | NA | NA |
| | β2m | 1.1 | <0.0001 | NA | NA |
| | HADMS Score | 31.01 | <0.0001 | 1.07 | NS |
| | HRS | 1.66 | NS | 4.52 | <0.0001 |
| | HADMS Score | 31.49 | <0.0001 | 1.65 | 0.01 |
| | IFM score | 2.16 | NS | 1.70 | 0.008 |
| | HADMS Score | 29.98 | <0.0001 | 1.63 | 0.01 |
| | t(4; 14) | 1.33 | .NS | 2.11 | 0.001 |
| | HADMS Score | 32.87 | <0.0001 | 1.63 | 0.01 |
| | del17p | 0.86 | NS | 2.31 | 0.001 |
| | HADMS Score | 29.04 | <0.0001 | 1.53 | 0.04 |
| | GPI | 1.36 | NS | 1.66 | 0.001 |
| | HADMS Score | 23.85 | <0.0001 | 1.40 | NS |
| | RS | 1.64 | NS | 1.81 | <0.0001 |
| | HADMS Score | 25.49 | <0.0001 | 1.50 | 0.05 |
| | DM Score | 1.56 | NS | 1.72 | 0.007 |
| | HADMS Score | 25.52 | <0.0001 | 1.33 | NS |
| | HA Score | 1.49 | NS | 1.76 | 0.006 |
| Multivariate COX analysis - Overall survival | HADMS Score | 32.90 | <0.0001 | 0.73 | NS |
| | β2m | 1.1 | <0.0001 | NA | NA |
| | ISS | 1.1 | NS | NA | NA |
| | HRS | 1.12 | NS | 3.75 | <0.0001 |

TABLE 4-continued

Cox univariate and multivariate analysis
of OS in HM and TT2 patients' cohorts.

| Pronostic variable | HM Cohort OAS | | TT2 Cohort OAS | |
|---|---|---|---|---|
| | Proportional hazard ratio | P-value | Proportional hazard ratio | P-value |
| IFM score | 1.1 | NS | 0.88 | NS |
| t(4; 14) | 1.42 | NS | 2.05 | .004 |
| del17p | 0.44 | NS | 2.31 | .001 |
| GPI | 0.73 | NS | 1.20 | NS |
| RS | 1.44 | NS | 0.98 | NS |
| DM Score | 1.1 | NS | 1.20 | NS |
| HA Score | 0.71 | NS | 1.62 | 0.02 |

The prognostic factors were tested as single variable or multi variables using Cox-model. P-values and the hazard ratios (HR) are shown. NS, Not significant at a 5% threshold; GPI, gene expression based proliferation index; ISS, International Staging System; HRS, high-risk score; IFM, Intergroupe Francophone du Myélome; DM score, DNA Methylation score, HA score, Histone Acetylation score, Serum concentration of β2m and albumin are not available for UAMS TT2 patients. NA, Not available.

HADMS Score is Predictive of Myeloma Cell Sensitivity to DNMTi and HDACi Combination.

The efficacy of HADMS score to predict sensitivity of myeloma cells sensitivity to DNMTi and HDACi combination treatment was investigated using primary MMC of patients co-cultured with their bone marrow microenvironment in vitro (Mahtouk, 2004; Moreaux, 2013; Moreaux, 2012; Moreaux, 2013). MMC of patients with a high HADMS score (n=5) were significantly more sensitive (3.4 fold) to decitabine and TSA combination than MMC of patients with a low HADMS score (n=5) (FIG. 4A). The inventors confirmed these results using another DNMTi and HDACi association. Primary MMCs of patients with a high HADMS score (n=5) exhibited a significant 1.7 higher sensitivity to clinical grade inhibitors 5-azacitidine/SAHA combination than MMC of patients with a low HADMS score (n=7) (FIG. 4B).

MMC of Patients with Low HADMS Score Value are Characterized by Mature BMPC Gene Signature whereas Patients with High HADMS Score have a Proliferating Plasmablastic Gene Signature.

In order to identify if different gene signatures could be identified comparing high HADMS score and low HADMS score groups, the inventors performed a GSEA analysis. MMC of patients with a low HADMS score displayed a significant enrichment in genes associated with normal mature BMPCs (gene set: ZHAN MULTIPLE MYELOMA DN, P=0.01, Table 5) and bone microenvironment dependence (gene sets: VILIMAS NOTCH1 TARGETS UP, ZHENG IL22 SIGNALING UP, AMIT EGF RESPONSE 120 HELA and RUTELLA RESPONSE TO HGF, P<0.02, Tables 6, 7, 8 and 9). At the opposite, MMCs of patients with a high HADMS score exhibited a significant enrichment in genes associated with proliferating plasmablastic progenitors (gene sets: MOREAUX MULTIPLE MYELOMA BY TACI DN, WHITFIELD CELL CYCLE S, P<0.01, Tables 10 and 11), IFN regulated genes (gene sets: REACTOME INTERFERON ALPHA BETA SIGNALING, RADAEVA RESPONSE TO IFNA1 UP and DER IFN BETA RESPONSE UP, P<0.01, Table 12, 13 and 14) and transcription (gene set: REACTOME TRANSCRIPTION, P<0.0001, Table 15). Investigating the HADMS score in normal plasma cell differentiation, HADMS score value was significantly higher in preplasmablasts (PrePB, P=0.05) and plasmablasts (PB, P=0.01) compared to memory B (MB) cells (FIG. 5). Early plasma cells have the highest score (P<0.001) and the HADMS score decreased drastically to the lowest value in mature BMPC (P<0.001) (FIG. 5).

TABLE 5

Genes set enrichment analysis revealed a significant overrepresentation of the ZHAN MULTIPLE MYELOMA DN set in low HADMS score patients compared to high HADMS score patients (P = 0.01).

| PROBE | GENE SYMBOL | RANK METRIC SCORE | RUNNING ES | CORE ENRICHMENT |
|---|---|---|---|---|
| PYGL | PYGL | 0.3619278371334076 | 0.07115942 | Yes |
| ITGB2 | ITGB2 | 0.3106897175312042 | 0.12719311 | Yes |
| S100A9 | S100A9 | 0.2768969237804413 | 0.1726828 | Yes |
| S100A12 | S100A12 | 0.25916585326194763 | 0.2160441 | Yes |
| WNT10B | WNT10B | 0.25076597929000854 | 0.26003012 | Yes |
| LST1 | LST1 | 0.24418431520462036 | 0.30363056 | Yes |
| AIF1 | AIF1 | 0.23883675038814545 | 0.34571996 | Yes |
| CXCL12 | CXCL12 | 0.23033247888088226 | 0.38202515 | Yes |
| CEBPD | CEBPD | 0.22803567349910736 | 0.42358118 | Yes |
| PRKAR2B | PRKAR2B | 0.21592438220977783 | 0.4545348 | Yes |
| LYZ | LYZ | 0.20603586733341217 | 0.48262537 | Yes |
| CD24 | CD24 | 0.2056848704814911 | 0.5227389 | Yes |
| DPYSL2 | DPYSL2 | 0.15517657995224 | 0.4734923 | Yes |
| IGF2BP3 | IGF2BP3 | 0.15381208062171936 | 0.5013209 | Yes |
| LCN2 | LCN2 | 0.15194584429264069 | 0.52604353 | Yes |
| ALDH1A1 | ALDH1A1 | 0.1436985582113266 | 0.53681916 | Yes |
| HNMT | HNMT | 0.14163549244403840 | 0.5599644 | Yes |
| A2M | A2M | 0.13225819170475006 | 0.56392044 | Yes |
| CTSH | CTSH | 0.13221798837184906 | 0.5897713 | Yes |
| APOC1 | APOC1 | 0.13114511966705322 | 0.6124445 | Yes |
| PF4 | PF4 | 0.12961214780807495 | 0.63504356 | Yes |
| PLA2G7 | PLA2G7 | 0.12095429003238678 | 0.6436146 | Yes |
| PF4V1 | PF4V1 | 0.1105586364865303 | 0.6471691 | Yes |
| APOE | APOE | 0.10622140765190125 | 0.65785354 | Yes |
| VCAM1 | VCAM1 | 0.09820647537708282 | 0.65988433 | Yes |

TABLE 6

Genes set enrichment analysis revealed a significant overrepresentation of the VILIMAS NOTCH1 TARGETS UP set in low HADMS score patients compared to high HADMS score patients (P = 0.007).

| PROBE | GENE SYMBOL | RANK METRIC SCORE | RUNNING ES | CORE ENRICHMENT |
|---|---|---|---|---|
| GATA3 | GATA3 | 0.30586645007133484 | 0.0816429 | Yes |
| RRAS2 | RRAS2 | 0.28479474782943726 | 0.15764606 | Yes |
| CD74 | CD74 | 0.26544249057769775 | 0.22896256 | Yes |
| DTX1 | DTX1 | 0.26188379526138306 | 0.30266726 | Yes |
| BCL2A1 | BCL2A1 | 0.24331431090831757 | 0.3600639 | Yes |
| THY1 | THY1 | 0.24279563128948212 | 0.4300697 | Yes |
| CD80 | CD80 | 0.2079179733991623 | 0.45193675 | Yes |
| LCK | LCK | 0.18203873932361603 | 0.46791258 | Yes |
| BIRC3 | BIRC3 | 0.17756520211696625 | 0.51153034 | Yes |
| CCR7 | CCR7 | 0.17335079610347748 | 0.5546125 | Yes |
| GZMA | GZMA | 0.17217615246772766 | 0.60259527 | Yes |

TABLE 7

Genes set enrichment analysis revealed a significant overrepresentation of the ZHENG IL22 SIGNALING UP set in low HADMS score patients compared to high HADMS score patients (P = 0.007).

| PROBE | GENE SYMBOL | RANK METRIC SCORE | RUNNING ES | CORE ENRICHMENT |
|---|---|---|---|---|
| CFD | CFD | 0.3332250714302063 | 0.08130651 | Yes |
| ARG1 | ARG1 | 0.3094353675842285 | 0.15615763 | Yes |
| PTX3 | PTX3 | 0.2970482110977173 | 0.22765689 | Yes |
| S100A9 | S100A9 | 0.2768969237804413 | 0.29247943 | Yes |
| HP | HP | 0.24530348181724548 | 0.33726114 | Yes |
| OLR1 | OLR1 | 0.23671993613243103 | 0.3889897 | Yes |
| RTN1 | RTN1 | 0.222052663564682 | 0.42836308 | Yes |
| CD14 | CD14 | 0.21896854043006897 | 0.48130947 | Yes |
| S100A8 | S100A8 | 0.19915771484375 | 0.50761944 | Yes |
| TTC9 | TTC9 | 0.19320820271968842 | 0.54746306 | Yes |
| ARRDC4 | ARRDC4 | 0.15338373184204102 | 0.5182652 | Yes |
| STXBP5L | STXBP5L | 0.15230797231197357 | 0.55394405 | Yes |
| SLC25A30 | SLC25A30 | 0.14586560428142548 | 0.57820314 | Yes |
| PF4 | PF4 | 0.12961214780807495 | 0.5708005 | Yes |
| CXCL6 | CXCL6 | 0.12492252886295319 | 0.5925112 | Yes |

TABLE 8

Genes set enrichment analysis revealed a significant overrepresentation of the AMIT EGF RESPONSE 120 HELA set in low HADMS score patients compared to high HADMS score patients (P = 0.01).

| PROBE | GENE SYMBOL | RANK METRIC SCORE | RUNNING ES | CORE ENRICHMENT |
|---|---|---|---|---|
| CYP1B1 | CYP1B1 | 0.348513543605780444 | 0.14713836 | Yes |
| PLAUR | PLAUR | 0.24194176495075226 | 0.21557675 | Yes |
| IL8 | IL8 | 0.234682902693748470 | 0.30890372 | Yes |
| CHST3 | CHST3 | 0.22654478251934052 | 0.39625484 | Yes |
| TGFA | TGFA | 0.1808186024427414 | 0.41380748 | Yes |
| IRS2 | IRS2 | 0.1508953720331192 | 0.4240509 | Yes |
| PHLDA1 | PHLDA1 | 0.14758902788162231 | 0.48134747 | Yes |
| SAT1 | SAT1 | 0.14673903584480286 | 0.5423769 | Yes |
| ANKRD57 | ANKRD57 | 0.14143554866313934 | 0.58999395 | Yes |

TABLE 9

Genes set enrichment analysis revealed a significant overrepresentation of the RUTELLA RESPONSE TO HGF set in low HADMS score patients compared to high HADMS score patients (P = 0.01).

| PROBE | GENE SYMBOL | RANK METRIC SCORE | RUNNING ES | CORE ENRICHMENT |
|---|---|---|---|---|
| C5AR1 | C5AR1 | 0.358140766620636 | 0.02953049 | Yes |
| CFD | CFD | 0.3332250714302063 | 0.055799164 | Yes |
| FPR1 | FPR1 | 0.3005441427230835 | 0.0749054 | Yes |

TABLE 9-continued

Genes set enrichment analysis revealed a significant overrepresentation of the RUTELLA RESPONSE TO HGF set in low HADMS score patients compared to high HADMS score patients (P = 0.01).

| PROBE | GENE SYMBOL | RANK METRIC SCORE | RUNNING ES | CORE ENRICHMENT |
|---|---|---|---|---|
| SLC2A3 | SLC2A3 | 0.2995496690273285 | 0.100186415 | Yes |
| S100A9 | S100A9 | 0.2768969237804413 | 0.11799232 | Yes |
| FYB | FYB | 0.27504757046699524 | 0.14074183 | Yes |
| FCN1 | FCN1 | 0.2612757384777069 | 0.15699755 | Yes |
| S100A12 | S100A12 | 0.25916585326194763 | 0.17771128 | Yes |
| SORL1 | SORL1 | 0.2563846707344055 | 0.19865389 | Yes |
| FNBP1 | FNBP1 | 0.24261964857578278 | 0.20754002 | Yes |
| AIF1 | AIF1 | 0.23883675038814545 | 0.22468361 | Yes |
| LMO2 | LMO2 | 0.23302534222602844 | 0.23762788 | Yes |
| MS4A6A | MS4A6A | 0.22917360067367554 | 0.25279692 | Yes |
| CEBPD | CEBPD | 0.22803567349910736 | 0.27041975 | Yes |
| CD14 | CD14 | 0.21896854043006897 | 0.28078684 | Yes |
| ADAM19 | ADAM19 | 0.20949435234069824 | 0.28734094 | Yes |
| SIGIRR | SIGIRR | 0.19608718156814575 | 0.28557757 | Yes |
| DAPP1 | DAPP1 | 0.1886170208454132 | 0.29036966 | Yes |
| TCF7L2 | TCF7L2 | 0.18315166234970093 | 0.29771394 | Yes |
| NDE1 | NDE1 | 0.17771971225738525 | 0.30320895 | Yes |
| NCOA1 | NCOA1 | 0.17465053498744965 | 0.3126174 | Yes |
| F2RL1 | F2RL1 | 0.17231358587741852 | 0.32391486 | Yes |
| CDKN1C | CDKN1C | 0.16997265815734863 | 0.33455113 | Yes |
| SPTLC2 | SPTLC2 | 0.16576433181762695 | 0.341587 | Yes |
| KLF10 | KLF10 | 0.16473393142223358 | 0.3545628 | Yes |
| CFP | CFP | 0.16449259221553802 | 0.36775002 | Yes |
| LRRK1 | LRRK1 | 0.16356340050697327 | 0.3808588 | Yes |
| TREM1 | TREM1 | 0.15977086126804352 | 0.38831607 | Yes |
| DPYSL2 | DPYSL2 | 0.15517657995224 | 0.3916767 | Yes |
| NR4A2 | NR4A2 | 0.15331326425075553 | 0.39974797 | Yes |
| NRG1 | NRG1 | 0.14798858761787415 | 0.40157476 | Yes |
| LTB4R | LTB4R | 0.1447547972202301 | 0.4066057 | Yes |
| SLC16A5 | SLC16A5 | 0.13600145280361176 | 0.39768505 | Yes |
| CHPT1 | CHPT1 | 0.13519573211669922 | 0.40608168 | Yes |
| LILRB2 | LILRB2 | 0.13153131306171417 | 0.40767854 | Yes |
| MAFB | MAFB | 0.12620945274829865 | 0.40674004 | Yes |
| SEPT9 | SEPT9 | 0.12541623413562775 | 0.41570213 | Yes |
| MAP4K4 | MAP4K4 | 0.12064750492572784 | 0.41823488 | Yes |
| RASGRP2 | RASGRP2 | 0.12002833187580109 | 0.42766947 | Yes |
| CD163 | CD163 | 0.11745651066303253 | 0.43340993 | Yes |
| ACPP | ACPP | 0.11506164073944092 | 0.4387165 | Yes |
| FCER1A | FCER1A | 0.11289910972118378 | 0.44523138 | Yes |
| ZNF395 | ZNF395 | 0.11033166944980621 | 0.45037052 | Yes |
| HLA-DQA1 | HLA-DQA1 | 0.10554853826761246 | 0.44838372 | Yes |
| PLEKHA5 | PLEKHA5 | 0.10223544389009476 | 0.44889894 | Yes |
| DPEP2 | DPEP2 | 0.10112230479717255 | 0.4558107 | Yes |

TABLE 10

Genes set enrichment analysis revealed a significant overrepresentation of the MOREAUX MULTIPLE MYELOMA BY TACI DN set in high HADMS score patients compared to low HADMS score patients (P < 0.0001).

| PROBE | GENE SYMBOL | RANK METRIC SCORE | RUNNING ES | CORE ENRICHMENT |
|---|---|---|---|---|
| MATR3 | MATR3 | −0.07275018095970154 | −0.6754449 | Yes |
| NUDCD2 | NUDCD2 | −0.08143609762191772 | −0.6673385 | Yes |
| NASP | NASP | −0.09491787105798721 | −0.6665999 | Yes |
| PAPD4 | PAPD4 | −0.10570180416107178 | −0.6483204 | Yes |
| RNF111 | RNF111 | −0.1149410605430603 | −0.62537616 | Yes |
| DDX31 | DDX31 | −0.12075252830982208 | −0.5895196 | Yes |
| ZNF567 | ZNF567 | −0.1243547722697258 | −0.5481924 | Yes |
| FLJ39632 | FLJ39632 | −0.13411782681941986 | −0.51337713 | Yes |
| DENND4A | DENND4A | −0.1658760905265808 | −0.48896423 | Yes |
| IREB2 | IREB2 | −0.17003612220287323 | −0.4272409 | Yes |
| MET | MET | −0.17687758803367615 | −0.3654088 | Yes |
| MYLIP | MYLIP | −0.1833156794309616 | −0.30020893 | Yes |
| TYMS | TYMS | −0.19542764127254486 | −0.23516361 | Yes |
| MCM2 | MCM2 | −0.20087213814258575 | −0.16144156 | Yes |
| CHEK1 | CHEK1 | −0.23729786276817322 | −0.08723888 | Yes |
| PAPOLA | PAPOLA | −0.26489123702049255 | 0.007963604 | Yes |

TABLE 11

Genes set enrichment analysis revealed a significant overrepresentation of the WHITFIELD CELL CYCLE S set in high HADMS score patients compared to low HADMS score patients (P = 0.002).

| PROBE | GENE SYMBOL | RANK METRIC SCORE | RUNNING ES | CORE ENRICHMENT |
|---|---|---|---|---|
| HIST1H2BC | HIST1H2BC | −0.12150858342647552 | −0.60519737 | Yes |
| PILRB | PILRB | −0.12402009218931198 | −0.58559793 | Yes |
| MAN1A2 | MAN1A2 | −0.1417795717716217 | −0.5867501 | Yes |
| ATAD2 | ATAD2 | −0.14950694143772125 | −0.56747854 | Yes |
| ESCO2 | ESCO2 | −0.1507851630449295 | −0.54134536 | Yes |
| PHIP | PHIP | −0.1666911095380783 | −0.52446014 | Yes |
| RRM2 | RRM2 | −0.18613113462924957 | −0.5047358 | Yes |
| TYMS | TYMS | −0.19542764127254486 | −0.47409338 | Yes |
| CPNE8 | CPNE8 | −0.19561581313610077 | −0.43657154 | Yes |
| HIST3H2A | HIST3H2A | −0.19778208434581757 | −0.39954406 | Yes |
| HELLS | HELLS | −0.20591014623641968 | −0.3639134 | Yes |
| BRIP1 | BRIP1 | −0.2078172266483307 | −0.3244931 | Yes |
| HIST1H4C | HIST1H4C | −0.21614468097686768 | −0.28734356 | Yes |
| UBE2T | UBE2T | −0.22249646484851837 | −0.24714345 | Yes |
| TOP2A | TOP2A | −0.23342227935791016 | −0.20506296 | Yes |
| IFIT1 | IFIT1 | −0.3525208830833435 | −0.15163203 | Yes |
| HIST1H2AM | HIST1H2AM | −0.3690810799598694 | −0.080634885 | Yes |
| HIST1H4H | HIST1H4H | −0.4202048182487488 | 2.0023435E−8 | Yes |

TABLE 12

Genes set enrichment analysis revealed a significant overrepresentation of the REACTOME INTERFERON ALPHA BETA SIGNALING set in high HADMS score patients compared to low HADMS score patients (P = 0.002).

| PROBE | GENE SYMBOL | RANK METRIC SCORE | RUNNING ES | CORE ENRICHMENT |
|---|---|---|---|---|
| OAS3 | OAS3 | −0.22055576741695404 | −0.7068872 | Yes |
| USP18 | USP18 | −0.26444268226623535 | −0.63302946 | Yes |
| IFIT3 | IFIT3 | −0.2971442639827728 | −0.5408215 | Yes |
| IFI27 | IFI27 | −0.30257943272590637 | −0.4429843 | Yes |
| OAS1 | OAS1 | −0.3027102053165436 | −0.34465006 | Yes |
| IFI6 | IFI6 | −0.3176177442073822 | −0.24238227 | Yes |
| IFIT1 | IFIT1 | −0.3525208830833435 | −0.12832178 | Yes |
| ISG15 | ISG15 | −0.39782193303108215 | 4.545678E−4 | Yes |

TABLE 13

Genes set enrichment analysis revealed a significant overrepresentation of the RADAEVA RESPONSE TO IFNA1 UP set in high HADMS score patients compared to low HADMS score patients (P = 0.004).

| PROBE | GENE SYMBOL | RANK METRIC SCORE | RUNNING ES | CORE ENRICHMENT |
|---|---|---|---|---|
| IFI44L | IFI44L | −0.24639743566513062 | −0.68106884 | Yes |
| IFI44 | IFI44 | −0.2476646453142166 | −0.60571516 | Yes |
| IFI27 | IFI27 | −0.30257943272590637 | −0.52133197 | Yes |
| OAS1 | OAS1 | −0.3027102053165436 | −0.4289525 | Yes |
| IFI6 | IFI6 | −0.3176177442073822 | −0.33293292 | Yes |
| RSAD2 | RSAD2 | −0.3443400263786316 | −0.2280764 | Yes |
| IFIT1 | IFIT1 | −0.3525208830833435 | −0.12049597 | Yes |
| ISG15 | ISG15 | −0.39782193303108215 | 4.5454444E−4 | Yes |

TABLE 14

Genes set enrichment analysis revealed a significant overrepresentation of the DER IFN BETA RESPONSE UP set in high HADMS score patients compared to low HADMS score patients (P < 0.0001).

| PROBE | GENE SYMBOL | RANK METRIC SCORE | RUNNING ES | CORE ENRICHMENT |
|---|---|---|---|---|
| TEAD1 | TEAD1 | −0.1300404965877533 | −0.5568645 | Yes |
| PLOD2 | PLOD2 | −0.13836008310317993 | −0.5350312 | Yes |

TABLE 14-continued

Genes set enrichment analysis revealed a significant overrepresentation of the DER IFN BETA RESPONSE UP set in high HADMS score patients compared to low HADMS score patients (P < 0.0001).

| PROBE | GENE SYMBOL | RANK METRIC SCORE | RUNNING ES | CORE ENRICHMENT |
|---|---|---|---|---|
| MAP1B | MAP1B | −0.13904088735580444 | −0.503463 | Yes |
| TRIM22 | TRIM22 | −0.16718308627605438 | −0.49792445 | Yes |
| HIF1A | HIF1A | −0.2176475077867508 | −0.4826493 | Yes |
| B2M | B2M | −0.23652824759483337 | −0.4340078 | Yes |
| IFI44 | IFI44 | −0.2476646453142166 | −0.37934482 | Yes |
| IFIT3 | IFIT3 | −0.2971442639827728 | −0.3172273 | Yes |
| OAS1 | OAS1 | −0.3027102053165436 | −0.24719761 | Yes |
| IFI6 | IFI6 | −0.3176177442073822 | −0.1739135 | Yes |
| IFIT1 | IFIT1 | −0.3525208830833435 | −0.09201994 | Yes |
| ISG15 | ISG15 | −0.39782193303108215 | 4.560307E−4 | Yes |

TABLE 15

Genes set enrichment analysis revealed a significant overrepresentation of the REACTOME TRANSCRIPTION set in high HADMS score patients compared to low HADMS score patients (P < 0.0001).

| PROBE | GENE SYMBOL | RANK METRIC SCORE | RUNNING ES | CORE ENRICHMENT |
|---|---|---|---|---|
| HIST1H2AE | HIST1H2AE | −0.11173597723245621 | −0.6660398 | Yes |
| HIST1H2BC | HIST1H2BC | −0.12150858342647552 | −0.63995767 | Yes |
| POU2F1 | POU2F1 | −0.131466805934906 | −0.6092625 | Yes |
| POLR3B | POLR3B | −0.14802579581737518 | −0.5762758 | Yes |
| HIST1H2AD | HIST1H2AD | −0.19305670261383057 | −0.547694 | Yes |
| HIST1H3D | HIST1H3D | −0.1993476301431656 | −0.47697288 | Yes |
| HIST1H4C | HIST1H4C | −0.21614468097686768 | −0.40569103 | Yes |
| HIST2H2BE | HIST2H2BE | −0.2228573113679886 | −0.32577235 | Yes |
| HIST1H3H | HIST1H3H | −0.2398541271686554 | −0.24203466 | Yes |
| PAPOLA | PAPOLA | −0.26489123702049255 | −0.14853144 | Yes |
| HIST1H4H | HIST1H4H | −0.4202048182487488 | 1.2529199E−8 | Yes |

Discussion

In this study, the inventors reported a GEP-based HADMS score that allows identification of high-risk patients associated with MMC's higher sensitivity to HDACi/DNMTi combination in vitro. Since HDACi/DNMTi combination was well tolerated (Bots, 2009), shown promising activity in cancers including haematological malignancies (Bots, 2009; Fandy, 2009; Zhang, 2009; Juergens, 2011) and have potential therapeutic value in MM (Matthews, 2013), the HADMS score could enable the identification of MM patients who could benefit from this treatment.

Among the 375 genes deregulated by decitabine and TSA in myeloma cell lines, 48 genes were also found to be deregulated after TSA treatment (Moreaux, 2013). 16 genes were communally deregulated by decitabine (Moreaux, 2012) and decitabine/TSA treatment. The inventors identified an overlap of 5 genes whose expression was affected by decitabine, TSA or decitabine/TSA (Tables 16, 17 and 18). Mainly deregulation of IFN-regulated genes was shared between decitabine and decitabine/TSA combined treatment (Moreaux, 2012). 85 genes were identified in common in our study and the study of Heller et at (Table 19). Thus, 80% of the decitabine/TSA combination deregulated genes were not found to be impacted by decitabine or TSA treatment alone in MMC. Cooperation between histone modifications and DNA methylation is important for the establishment of global epigenetic patterns as well as loci-specific gene regulation (Cedar, 2009). This crosstalk can be mediated by biochemical interactions between SET domain histone methyltransferases and DNA methyltransferases (Cedar, 2009). Interestingly, HADMS score is significantly upregulated in the t(4; 14) subgroup characterized by the overexpression of the SET domain histone methyltransferase MMSET (FIG. 6).

The 96 genes, building HADMS score, include 42 genes associated with a bad prognosis and 54 associated with a good prognosis (FIG. 1). Among these genes, some of them could highlight pathways involved in MM biology and sensitivity to DNMTi/HDACi combination. Since a significant enrichment in genes associated with proliferation was identified in MMC of patients with high HADMS score value, the higher sensitivity of high HADMS score patients to DNMTi/HDACi combination could be explained by the fact that incorporation of DNMTi into DNA is restricted to cell cycling cells (Hollenbach, 2010). Furthermore, HDACi have been shown to induce G1 cell cycle arrest through dephosphorylation of retinoblastoma protein and increase expression of p53 and p21 (Lavelle, 2001; Mitsiades, 2003; Neri, 2012). Using methylation-specific PCR, several studies have identified hypermethylation of tumor suppressor genes including cyclin dependent kinases inhibitors (CDKI, p15 and p16) and p14 (Braggio, 2010; Takada, 2005; Mateos, 2002). The inventors reported DNMTi/HDACi treatment induced p21 and p57 CDKI expression in MMC (Table A) and their expression is associated with a good prognosis in MM patients (Table A). The inventors identified also an induction of Cdc14b expression, another good prognostic gene. Cdc14b has been proposed to play multiple functions during the cell cycle (Mocciaro, 2010). In yeast, Cdc14 protein phosphatase is essential for the inactivation of mitotic CDK and mitotic exit (Mocciaro, 2010; Wei, 2011). Cells of Cdc14b-deficient mice displayed proliferative defects and increased senescence both in vitro and in vivo (Wei, 2011). More recently, it was reported that the lack of Cdc14b results in a significant increased transcription of cell cycle specific genes including A and B-type cyclins. At the opposite, ectopic expression of Cdc14b results in a significant repression of cell cycle genes (Guillamot, 2011). Among the good prognostic genes induced by these epigenetic drugs, the inventors identify EGF negative regulator (ERRFI1 also known as Mig-6). ERRFI1 deletion in mice has been reported to activate EGFR and sustain MAPK signaling, resulting in tumor development (Zhang, 2007; Anastasi, 2007; Ferby, 2006). ERRFI1 deletion, mutation or downregulation have been frequently identified in glioblastoma, lung and breast cancers (Anastasi, 2005; Ichimura, 2008; Ying, 2010). In glioblastoma, ERRFI1 overexpression was shown to decrease proliferation, the binding of EGFR with STX8 and drive internalized EGFR to endosomes for degradation. In contrast, ERRFI1 depletion resulted in increased tumor invasion (Ying, 2010). Furthermore, a recent study demonstrated that ERRFI1 expression is upregulated during the senescence process (Xie, 2013). The inventors have previously demonstrated that the EGF/EGF-receptor family is involved in the biology of MM (Mahtouk, 2006; Mahtouk, 2005; Mahtouk, 2004) acting as myeloma cell growth factors. A pan-ErbB inhibitor induced strong apoptosis of MMC co-cultured with their bone marrow microenvironment in vitro and combination with dexamethasone or anti-IL-6 antibody demonstrated additive effects (Mahtouk, 2004). Thus, DNMTi/HDACi combination could be useful to induce the expression of major tumor suppressor genes in MMC.

According to the proliferation gene signature, high HADMS score patients are characterized by an overexpression of genes related to transcription including histone cluster genes (Table 15). Core histone proteins must be synthesized rapidly during the brief S-phase when a cell is dividing (Harris, 1991). As a result, the histone mRNAs are highly cell-cycle regulated, increasing 35-fold as cell enter S-phase and decreasing again at the end of S-phase (Harris, 1991). All together, these data could clarify why high HADMS score patients, distinguished by an active growth, can be efficiently targeted by the upregulation of HDACi/DNMTi targeted genes and especially the 54 with a good prognostic value.

At the opposite, MMC of patients with a low HADMS score could be in a more quiescent stage. GSEA analysis revealed that MMC of patients with a low HADMS score showed a signature resembling mature BMPC associated with bone marrow microenvironment dependence underlined by a significant enrichment in intercellular communication signal pathways (Tables 5 to 9). In contrast, MMC of patients with a high HADMS score are characterized by a signature sharing similarities with less differentiated proliferating plasmablastic progenitors (Tables 10 to 15). Recently, it was described, within the bone marrow of MM patients, the existence of a progenitor organization recapitulating the different maturation stages of plasma cell differentiation (Jourdan, 2011; Jourdan, 2009) and associated with proteasome inhibitor resistance (Leung-Hagesteijn, 2013; Chaidos, 2013). MMC progenitors including B cells and preplasmablasts were found to survive to proteasome inhibitors and to be significantly enriched in myeloma patients refractory to bortezomib treatment. These Xbp1s negative preblasmablastic cells are characterized by a diminished endoplasmic reticulum (ER) stress and thus resistance to proteasome inhibitors since they have not committed to high Ig production (Leung-Hagesteijn, 2013; Orlowski, 2013). Furthermore, plasmablastic progenitors have been described to overexpress epigenetic regulators, compared to mature plasma cells, suggesting that MMC transitions in plasma cell differentiation stages could be linked to epigenetic plasticity (Chaidos, 2013). According to the GSEA results, HADMS score was significantly higher in preplasmablasts, plasmablasts and early plasma cells compared to normal mature BMPC (FIG. 5). Thus, HDACi/DNMTi combined treatment could have a therapeutic interest to target tumor progenitors that contribute to treatment failure in MM.

Recent clinical trials suggested promising activity of HDACi/DNMTi combination in MDS, AML (Bots, 2009; Fandy, 2009; Zhang, 2009) and refractory advanced non-small cell lung cancer (Juergens, 2011). In MM, clinical trials evaluating DNMTi or HDACi are ongoing and their combination resulted in a significant results in Vk*MYC transgenic MM mouse model (Matthews, 2013). In the current study, the inventors reported a new score to predict the MM cell sensitivity to DNMTi and HDACi combination that could be useful identifying patients who could benefit from combination of epigenetic therapies.

TABLE 16

Genes communally overexpressed in decitabine and decitabine/TSA treated HMCLs

| UNIQID | Gene | Banding |
|---|---|---|
| 200696_s_at | GSN | 9q33 |
| 201243_s_at | ATP1B1 | 1q24 |
| 201631_s_at | IER3 | 6p21.3 |
| 202086_at | MX1 | 21q22.3 |
| 202411_at | IFI27 | 14q32 |
| 203964_at | NMI | 2p24.3-q21.3 |
| 204141_at | TUBB2 | 6p25 |
| 205483_s_at | G1P2 | 1p36.33 |
| 205552_s_at | OAS1 | 12q24.1 |
| 209122_at | ADFP | 9p22.1 |
| 209969_s_at | STAT1 | 2q32.2 |
| 210387_at | HIST1H2BG | 6p21.3 |
| 210437_at | MAGEA9 | Xq28 |
| 211990_at | HLA-DPA1 | 6p21.3 |
| 218543_s_at | PARP12 | 7q34 |
| 223484_at | NMES1 | 15q21.1 |
| 224917_at | MIRN21 | — |
| 227609_at | EPSTI1 | 13q13.3 |
| 230000_at | C17orf27 | 17q25.3 |
| 235700_at | CT45-2 | Xq26.3 |
| 238825_at | ACRC | Xq13.1 |

TABLE 17

Genes communally overexpressed in TSA and decitabine/TSA treated HMCLs

| UNIQID | Gene | Banding |
|---|---|---|
| 200696_s_at | GSN | 9q33 |
| 201012_at | ANXA1 | 9q12-q21.2\|9q12-q21.2 |
| 201137_s_at | HLA-DPB1 | 6p21.3 |
| 202838_at | FUCA1 | 1p34 |
| 203355_s_at | PSD3 | 8pter-p23.3 |
| 203413_at | NELL2 | 12q13.11-q13.12 |
| 203695_s_at | DFNA5 | 7p15 |
| 203854_at | IF | 4q25 |
| 204415_at | G1P3 | 1p35 |
| 204563_at | SELL | 1q23-q25 |
| 205249_at | EGR2 | 10q21.1 |
| 205352_at | SERPINI1 | 3q26.1 |

TABLE 17-continued

Genes communally overexpressed in TSA and decitabine/TSA treated HMCLs

| UNIQID | Gene | Banding |
|---|---|---|
| 205552_s_at | OAS1 | 12q24.1 |
| 206310_at | SPINK2 | 4q12 |
| 206385_s_at | ANK3 | 10q21 |
| 208894_at | HLA-DRA | 6p21.3 |
| 209198_s_at | SYT11 | 1q21.2 |
| 209462_at | APLP1 | 19q13.1 |
| 209848_s_at | SILV | 12q13-q14 |
| 209906_at | C3AR1 | 12p13.31 |
| 209969_s_at | STAT1 | 2q32.2 |
| 210432_s_at | SCN3A | 2q24 |
| 210538_s_at | BIRC3 | 11q22 |
| 211685_s_at | NCALD | 8q22-q23 |
| 211990_at | HLA-DPA1 | 6p21.3 |
| 212464_s_at | FN1 | 2q34 |
| 212636_at | QKI | 6q26-27 |
| 212998_x_at | HLA-DQB1 | 6p21.3 |
| 213106_at | ATP8A1 | 4p14-p12 |
| 213317_at | CLIC5 | 6p12.1-21.1 |
| 213361_at | TDRD7 | 9q22.33 |
| 214079_at | DHRS2 | 14q11.2 |
| 215193_x_at | HLA-DRB1 | 6p21.3 |
| 216331_at | ITGA7 | 12q13 |
| 218501_at | ARHGEF3 | 3p21-p13 |
| 218678_at | NES | 1q23.1 |
| 219209_at | IFIH1 | 2p24.3-q24.3 |
| 223218_s_at | NFKBIZ | 3p12-q12 |
| 223484_at | NMES1 | 15q21.1 |
| 224701_at | PARP14 | 3q21.1 |
| 225123_at | SESN3 | 11q21 |
| 225688_s_at | PHLDB2 | 3q13.2 |
| 225842_at | — | — |
| 226269_at | GDAP1 | 8q21.11 |
| 226281_at | DNER | 2q36.3 |
| 226725_at | — | — |
| 228152_s_at | FLJ31033 | 4q32.3 |
| 228260_at | ELAVL2 | 9p21 |
| 228726_at | SERPINB1 | 6p25 |
| 229973_at | C1orf173 | 1p31.1 |
| 230233_at | RASGEF1B | 4q21.3 |
| 238430_x_at | MGC19764 | 17q12 |
| 34408_at | RTN2 | 19q13.32 |

TABLE 18

Genes communally overexpressed in TSA, decitabine and decitabine/TSA treated HMCLs

| UNIQID | Gene | Banding |
|---|---|---|
| 200696_s_at | GSN | 9q33 |
| 205552_s_at | OAS1 | 12q24.1 |
| 209969_s_at | STAT1 | 2q32.2 |
| 211990_at | HLA-DPA1 | 6p21.3 |
| 223484_at | NMES1 | 15q21.1 |

TABLE 19

Genes overexpressed in decitabine/TSA treated HMCLs in the study conducted by Heller G et al. and the current study

| UNIQID | Gene | Banding |
|---|---|---|
| 200696_s_at | GSN | 9q33 |
| 200799_at | HSPA1A | 6p21.3 |
| 200878_at | EPAS1 | 2p21-p16 |
| 201005_at | CD9 | 12p13.3 |
| 201041_s_at | DUSP1 | 5q34 |
| 201131_s_at | CDH1 | 16q22.1 |
| 201137_s_at | HLA-DPB1 | 6p21.3 |
| 201243_s_at | ATP1B1 | 1q24 |

TABLE 19-continued

Genes overexpressed in decitabine/TSA treated HMCLs in the study conducted by Heller G et al. and the current study

| UNIQID | Gene | Banding |
|---|---|---|
| 201416_at | SOX4 | 6p22.3 |
| 201427_s_at | SEPP1 | 5q31 |
| 201596_x_at | KRT18 | 12q13 |
| 201631_s_at | IER3 | 6p21.3 |
| 201694_s_at | EGR1 | 5q31.1 |
| 201939_at | PLK2 | 5q12.1-q13.2 |
| 201952_at | ALCAM | 3q13.1 |
| 202071_at | SDC4 | 20q12 |
| 202219_at | SLC6A8 | Xq28 |
| 202252_at | RAB13 | 1q21.2 |
| 202283_at | SERPINF1 | 17p13.1 |
| 202284_s_at | CDKN1A | 6p21.2 |
| 202411_at | IFI27 | 14q32 |
| 202436_s_at | CYP1B1 | 2p21 |
| 202668_at | EFNB2 | 13q33 |
| 202838_at | FUCA1 | 1p34 |
| 203130_s_at | KIF5C | 2q23.1 |
| 203153_at | IFIT1 | 10q25-q26 |
| 203186_s_at | S100A4 | 1q21 |
| 203404_at | ARMCX2 | Xq21.33-q22.2 |
| 203680_at | PRKAR2B | 7q22 |
| 203879_at | PIK3CD | 1p36.2 |
| 204141_at | TUBB2 | 6p25 |
| 204415_at | G1P3 | 1p35 |
| 205239_at | AREG | 4q13-q21 |
| 205249_at | EGR2 | 10q21.1 |
| 205352_at | SERPINI1 | 3q26.1 |
| 205569_at | LAMP3 | 3q26.3-q27 |
| 206310_at | SPINK2 | 4q12 |
| 206588_at | DAZL | 3p24.3 |
| 207030_s_at | CSRP2 | 12q21.1 |
| 208614_s_at | FLNB | 3p14.3 |
| 208886_at | H1F0 | 22q13.1 |
| 208937_s_at | ID1 | 20q11 |
| 209160_at | AKR1C3 | 10p15-p14 |
| 209198_s_at | SYT11 | 1q21.2 |
| 209306_s_at | SWAP70 | 11p15 |
| 209392_at | ENPP2 | 8q24.1 |
| 209459_s_at | ABAT | 16p13.2 |
| 209462_at | APLP1 | 19q13.1 |
| 209603_at | GATA3 | 10p15 |
| 209848_s_at | SILV | 12q13-q14 |
| 209969_s_at | STAT1 | 2q32.2 |
| 209993_at | ABCB1 | 7q21.1 |
| 210074_at | CTSL2 | 9q22.2 |
| 210095_s_at | IGFBP3 | 7p13-p12 |
| 210387_at | HIST1H2BG | 6p21.3 |
| 210437_at | MAGEA9 | Xq28 |
| 210538_s_at | BIRC3 | 11q22 |
| 210592_s_at | SAT | Xp22.1 |
| 210986_s_at | TPM1 | 15q22.1 |
| 211404_s_at | APLP2 | 11q23-q25|11q24 |
| 211538_s_at | HSPA2 | 14q24.1 |
| 211990_at | HLA-DPA1 | 6p21.3 |
| 212094_at | PEG10 | 7q21 |
| 212464_s_at | FN1 | 2q34 |
| 212473_s_at | MICAL2 | 11p15.3 |
| 212561_at | RAB6IP1 | 11p15.4 |
| 213348_at | CDKN1C | 11p15.5 |
| 213800_at | CFH | 1q32 |
| 214079_at | DHRS2 | 14q11.2 |
| 214440_at | NAT1 | 8p23.1-p21.3 |
| 214469_at | HIST1H2AE | 6p22.2-p21.1 |
| 214696_at | MGC14376 | 17p13.3 |
| 215193_x_at | HLA-DRB1 | 6p21.3 |
| 215440_s_at | BEXL1 | Xq22.1-q22.3 |
| 216331_at | ITGA7 | 12q13 |
| 216370_s_at | TKTL1 | Xq28 |
| 216379_x_at | CD24 | 6q21 |
| 217767_at | C3 | 19p13.3-p13.2 |
| 219403_s_at | HPSE | 4q21.3 |
| 219870_at | ATF7IP2 | 16p13.13 |
| 221555_x_at | CDC14B | 9q22.33 |
| 224583_at | COTL1 | 16q24.1 |
| 227530_at | AKAP12 | 6q24-q25 |

TABLE 19-continued

Genes overexpressed in decitabine/TSA treated HMCLs in the study conducted by Heller G et al. and the current study

| UNIQID | Gene | Banding |
|---|---|---|
| 228423_at | FLJ21159 | 4q32.1 |
| 34408_at | RTN2 | 19q13.32 |

REFERENCES

Throughout this application, various references describe the state of the art to which this invention pertains. The disclosures of these references are hereby incorporated by reference into the present disclosure.

1. Heuck C J, Mehta J, Bhagat T, et al. Myeloma is characterized by stage-specific alterations in DNA methylation that occur early during myelomagenesis. J Immunol. Mar. 15, 2013; 190(6):2966-2975.
2. Walker B A, Wardell C P, Chiecchio L, et al. Aberrant global methylation patterns affect the molecular pathogenesis and prognosis of multiple myeloma. Blood. Oct. 13, 2010.
3. Hollenbach P W, Nguyen A N, Brady H, et al. A comparison of azacitidine and decitabine activities in acute myeloid leukemia cell lines. PLoS One. 2010; 5(2):e9001.
4. Maes K, Menu E, Van Valckenborgh E, Van Riet I, Vanderkerken K, De Bruyne E. Epigenetic Modulating Agents as a New Therapeutic Approach in Multiple Myeloma. Cancers. 2013; 5(2):430-461.
5. Feng R, Ma H, Hassig C A, et al. KD5170, a novel mercaptoketone-based histone deacetylase inhibitor, exerts antimyeloma effects by DNA damage and mitochondrial signaling. Mol Cancer Ther. June 2008; 7(6):1494-1505.
6. Khan S B, Maududi T, Barton K, Ayers J, Alkan S. Analysis of histone deacetylase inhibitor, depsipeptide (FR901228), effect on multiple myeloma. Br J Haematol. April 2004; 125(2):156-161.
7. Lavelle D, Chen Y H, Hankewych M, DeSimone J. Histone deacetylase inhibitors increase p21(WAF1) and induce apoptosis of human myeloma cell lines independent of decreased IL-6 receptor expression. Am J Hematol. November 2001; 68(3):170-178.
8. Mitsiades C S, Mitsiades N S, McMullan C J, et al. Transcriptional signature of histone deacetylase inhibition in multiple myeloma: biological and clinical implications. Proc Natl Acad Sci USA. Jan. 13, 2004; 101(2):540-545.
9. Mitsiades N, Mitsiades C S, Richardson P G, et al. Molecular sequelae of histone deacetylase inhibition in human malignant B cells. Blood. May 15, 2003; 101(10):4055-4062.
10. Catley L, Weisberg E, Tai Y T, et al. NVP-LAQ824 is a potent novel histone deacetylase inhibitor with significant activity against multiple myeloma. Blood. Oct. 1, 2003; 102(7):2615-2622.
11. Kaiser M, Zavrski I, Sterz J, et al. The effects of the histone deacetylase inhibitor valproic acid on cell cycle, growth suppression and apoptosis in multiple myeloma. Haematologica. February 2006; 91(2):248-251.
12. Neri P, Bahlis N J, Lonial S. Panobinostat for the treatment of multiple myeloma. Expert Opin Investig Drugs. May 2012; 21(5):733-747.
13. Neri P, Tagliaferri P, Di Martino M T, et al. In vivo anti-myeloma activity and modulation of gene expression profile induced by valproic acid, a histone deacetylase inhibitor. Br J Haematol. November 2008; 143(4):520-531.
14. Minami J, Suzuki R, Mazitschek R, et al. Histone deacetylase 3 as a novel therapeutic target in multiple myeloma. Leukemia. Aug. 5, 2013.
15. Hideshima T, Mazitschek R, Santo L, et al. Induction of differential apoptotic pathways in multiple myeloma cells by class-selective histone deacetylase inhibitors. Leukemia. Oct. 22, 2013.
16. Zhang Q L, Wang L, Zhang Y W, et al. The proteasome inhibitor bortezomib interacts synergistically with the histone deacetylase inhibitor suberoylanilide hydroxamic acid to induce T-leukemia/lymphoma cells apoptosis. Leukemia. August 2009; 23(8):1507-1514.
17. Richardson P G, Schlossman R L, Alsina M, et al. PANORAMA 2: panobinostat in combination with bortezomib and dexamethasone in patients with relapsed and bortezomib-refractory myeloma. Blood. Oct. 3, 2013; 122(14):2331-2337.
18. San-Miguel J F, Richardson P G, Gunther A, et al. Phase Ib study of panobinostat and bortezomib in relapsed or relapsed and refractory multiple myeloma. J Clin Oncol. Oct. 10, 2013; 31(29):3696-3703.
19. Dimopoulos M, Siegel D S, Lonial S, et al. Vorinostat or placebo in combination with bortezomib in patients with multiple myeloma (VANTAGE 088): a multicentre, randomised, double-blind study. Lancet Oncol. October 2013; 14(11):1129-1140.
20. Moreno-Bost A, Szmania S, Stone K, et al. Epigenetic modulation of MAGE-A3 antigen expression in multiple myeloma following treatment with the demethylation agent 5-azacitidine and the histone deacetlyase inhibitor MGCD0103. Cytotherapy. May 2011; 13(5):618-628.
21. Matthews G M, Lefebure M, Doyle M A, et al. Preclinical screening of histone deacetylase inhibitors combined with ABT-737, rhTRAIL/MD5-1 or 5-azacytidine using syngeneic Vk*MYC multiple myeloma. Cell death & disease. 2013; 4:e798.
22. Bots M, Johnstone R W. Rational combinations using HDAC inhibitors. Clin Cancer Res. Jun. 15, 2009; 15(12):3970-3977.
23. Fandy T E, Herman J G, Kerns P, et al. Early epigenetic changes and DNA damage do not predict clinical response in an overlapping schedule of 5-azacytidine and entinostat in patients with myeloid malignancies. Blood. Sep. 24, 2009; 114(13):2764-2773.
24. Juergens R A, Wrangle J, Vendetti F P, et al. Combination epigenetic therapy has efficacy in patients with refractory advanced non-small cell lung cancer. Cancer discovery. December 2011; 1(7):598-607.
25. Moreaux J, Bruyer A, Veyrune J L, Goldschmidt H, Hose D, Klein B. DNA methylation score is predictive of myeloma cell sensitivity to 5-azacitidine. Br J Haematol. Nov. 13, 2013.
26. Moreaux J, Reme T, Leonard W, et al. Development of gene expression-based score to predict sensitivity of multiple myeloma cells to DNA methylation inhibitors. Mol Cancer Ther. December 2012; 11(12):2685-2692.
27. Moreaux J, Reme T, Leonard W, et al. Gene expression-based prediction of myeloma cell sensitivity to histone deacetylase inhibitors. Br J Cancer. Aug. 6, 2013; 109(3):676-685.
28. Gu Z J, Vos J D, Rebouissou C, et al. Agonist anti-gp130 transducer monoclonal antibodies are human myeloma cell survival and growth factors. Leukemia. 2000; 14(1):188-197.
29. Moreaux J, Klein B, Bataille R, et al. A high-risk signature for patients with multiple myeloma established from the molecular classification of human myeloma cell lines. Haematologica. April 2011; 96(4):574-582.

30. Rebouissou C, Wijdenes J, Autissier P, et al. A gp130 interleukin-6 transducer-dependent SCID model of human multiple myeloma. Blood. 1998; 91(12):4727-4737.

31. Tarte K, Zhang X G, Legouffe E, et al. Induced expression of B7-1 on myeloma cells following retroviral gene transfer results in tumor-specific recognition by cytotoxic T cells. J Immunol. 1999; 163(1):514-524.

32. Zhang X G, Gaillard J P, Robillard N, et al. Reproducible obtaining of human myeloma cell lines as a model for tumor stem cell study in human multiple myeloma. Blood. 1994; 83(12):3654-3663.

33. Hose D, Reme T, Hielscher T, et al. Proliferation is a central independent prognostic factor and target for personalized and risk-adapted treatment in multiple myeloma. Haematologica. January 2011; 96(1):87-95.

34. De Vos J, Thykjaer T, Tarte K, et al. Comparison of gene expression profiling between malignant and normal plasma cells with oligonucleotide arrays. Oncogene. 2002; 21(44):6848-6857.

35. Barlogie B, Tricot G, Rasmussen E, et al. Total therapy 2 without thalidomide in comparison with total therapy 1: role of intensified induction and posttransplantation consolidation therapies. Blood. Apr. 1, 2006; 107(7):2633-2638.

36. Kassambara A, Hose D, Moreaux J, et al. Genes with a spike expression are clustered in chromosome (sub)bands and spike (sub)bands have a powerful prognostic value in patients with multiple myeloma. Haematologica. April 2012; 97(4):622-630.

37. Xiong W, Wu X, Starnes S, et al. An analysis of the clinical and biologic significance of TP53 loss and the identification of potential novel transcriptional targets of TP53 in multiple myeloma. Blood. Nov. 15, 2008; 112(10):4235-4246.

38. Jourdan M, Caraux A, De Vos J, et al. An in vitro model of differentiation of memory B cells into plasmablasts and plasma cells including detailed phenotypic and molecular characterization. Blood. Dec. 10, 2009; 114(25):5173-5181.

39. Jourdan M, Caraux A, Caron G, et al. Characterization of a transitional preplasmablast population in the process of human B cell to plasma cell differentiation. J Immunol. Oct. 15, 2011; 187(8):3931-3941.

40. Heller G, Schmidt W M, Ziegler B, et al. Genome-wide transcriptional response to 5-aza-2'-deoxycytidine and trichostatin a in multiple myeloma cells. Cancer Res. Jan. 1, 2008; 68(1):44-54.

41. Mahtouk K, Jourdan M, De Vos J, et al. An inhibitor of the EGF receptor family blocks myeloma cell growth factor activity of HB-EGF and potentiates dexamethasone or anti-IL-6 antibody-induced apoptosis. Blood. Mar. 1, 2004; 103(5):1829-1837.

42. Cui X, Churchill G A. Statistical tests for differential expression in cDNA microarray experiments. Genome Biol. 2003; 4(4):210.

43. Subramanian A, Tamayo P, Mootha V K, et al. Gene set enrichment analysis: a knowledge-based approach for interpreting genome-wide expression profiles. Proc Natl Acad Sci USA. Oct. 25, 2005; 102(43):15545-15550.

44. Zhan F, Huang Y, Colla S, et al. The molecular classification of multiple myeloma. Blood. Sep. 15, 2006; 108(6):2020-2028.

45. Shaughnessy J D, Jr., Zhan F, Burington B E, et al. A validated gene expression model of high-risk multiple myeloma is defined by deregulated expression of genes mapping to chromosome 1. Blood. Mar. 15, 2007; 109(6):2276-2284.

46. Decaux O, Lode L, Magrangeas F, et al. Prediction of survival in multiple myeloma based on gene expression profiles reveals cell cycle and chromosomal instability signatures in high-risk patients and hyperdiploid signatures in low-risk patients: a study of the Intergroupe Francophone du Myelome. J Clin Oncol. Oct. 10, 2008; 26(29):4798-4805.

47. Reme T, Hose D, Theillet C, Klein B. Modeling risk stratification in human cancer. Bioinformatics. May 1, 2013; 29(9):1149-1157.

48. Cedar H, Bergman Y. Linking DNA methylation and histone modification: patterns and paradigms. Nat Rev Genet. May 2009; 10(5):295-304.

49. Braggio E, Maiolino A, Gouveia M E, et al. Methylation status of nine tumor suppressor genes in multiple myeloma. Int J Hematol. January 2010; 91(1):87-96.

50. Takada S, Morita K, Hayashi K, et al. Methylation status of fragile histidine triad (FHIT) gene and its clinical impact on prognosis of patients with multiple myeloma. Eur J Haematol. December 2005; 75(6):505-510.

51. Mateos M V, Garcia-Sanz R, Lopez-Perez R, et al. Methylation is an inactivating mechanism of the p16 gene in multiple myeloma associated with high plasma cell proliferation and short survival. Br J Haematol. September 2002; 118(4):1034-1040.

52. Mocciaro A, Schiebel E. Cdc14: a highly conserved family of phosphatases with non-conserved functions? J Cell Sci. Sep. 1, 2010; 123(Pt 17):2867-2876.

53. Wei Z, Peddibhotla S, Lin H, et al. Early-onset aging and defective DNA damage response in Cdc14b-deficient mice. Mol Cell Biol. April 2011; 31(7):1470-1477.

54. Guillamot M, Manchado E, Chiesa M, et al. Cdc14b regulates mammalian RNA polymerase II and represses cell cycle transcription. Scientific reports. 2011; 1:189.

55. Zhang X, Pickin K A, Bose R, Jura N, Cole P A, Kuriyan J. Inhibition of the EGF receptor by binding of MIG6 to an activating kinase domain interface. Nature. Nov. 29, 2007; 450(7170):741-744.

56. Anastasi S, Baietti M F, Frosi Y, Alema S, Segatto O. The evolutionarily conserved EBR module of RALT/MIG6 mediates suppression of the EGFR catalytic activity. Oncogene. Dec. 13, 2007; 26(57):7833-7846.

57. Ferby I, Reschke M, Kudlacek O, et al. Mig6 is a negative regulator of EGF receptor-mediated skin morphogenesis and tumor formation. Nat Med. May 2006; 12(5):568-573.

58. Anastasi S, Sala G, Huiping C, et al. Loss of RALT/MIG-6 expression in ERBB2-amplified breast carcinomas enhances ErbB-2 oncogenic potency and favors resistance to Herceptin. Oncogene. Jun. 30, 2005; 24(28):4540-4548.

59. Ichimura K, Vogazianou A P, Liu L, et al. 1p36 is a preferential target of chromosome 1 deletions in astrocytic tumours and homozygously deleted in a subset of glioblastomas. Oncogene. Mar. 27, 2008; 27(14):2097-2108.

60. Ying H, Zheng H, Scott K, et al. Mig-6 controls EGFR trafficking and suppresses gliomagenesis. Proc Natl Acad Sci USA. Apr. 13, 2010; 107(15):6912-6917.

61. Xie B, Zhao L, Chen H, Jin B, Mao Z, Yao Z. The mitogen-inducible gene-6 is involved in regulation of cellular senescence in normal diploid fibroblasts. Biol Cell. October 2013; 105(10):488-499.

62. Mahtouk K, Cremer F W, Reme T, et al. Heparan sulphate proteoglycans are essential for the myeloma cell growth activity of EGF-family ligands in multiple myeloma. Oncogene. Nov. 16, 2006; 25(54):7180-7191.

63. Mahtouk K, Hose D, Reme T, et al. Expression of EGF-family receptors and amphiregulin in multiple myeloma. Amphiregulin is a growth factor for myeloma cells. Oncogene. May 12, 2005; 24(21):3512-3524.

64. Harris M E, Bohni R, Schneiderman M H, Ramamurthy L, Schumperli D, Marzluff W F. Regulation of histone mRNA in the unperturbed cell cycle: evidence suggesting control at two posttranscriptional steps. Mol Cell Biol. May 1991; 11(5):2416-2424.

65. Leung-Hagesteijn C, Erdmann N, Cheung G, et al. Xbp1s-negative tumor B cells and pre-plasmablasts mediate therapeutic proteasome inhibitor resistance in multiple myeloma. Cancer Cell. Sep. 9, 2013; 24(3):289-304.

66. Chaidos A, Barnes C P, Cowan G, et al. Clinical drug resistance linked to interconvertible phenotypic and functional states of tumor-propagating cells in multiple myeloma. Blood. Jan. 10, 2013; 121(2):318-328.

67. Orlowski R Z. Why proteasome inhibitors cannot ERADicate multiple myeloma. Cancer Cell. Sep. 9, 2013; 24(3):275-277.

The invention claimed is:

1. A method of treating a patient able to respond to a combination treatment consisting of at least one histone deacetylase inhibitor (HDACi) with at least one DNA methyltransferase inhibitor (DNMTi), wherein said patient is suffering from multiple myeloma, comprising the steps of:
   a) identifying the patient able to respond to the combination treatment by performing the following steps:
      i) isolating a biological sample from said patient and measuring in said biological sample the expression level (ELi) of at least 42 genes selected from the group consisting of: ABCB1, ADAM28, ADFP, ANK3, ARRDC4, ATP1B1, BIRC4BP, C11orf32, C1orf38, CD24, CDC14B, CDC42EP3, CDH1, CDKN1A, CDKN1C, CFH, CLIC5, COTL1, CT45-2, CYP1B1, DDR1, DDX58, DHRS2, DKFZp434C0328, DUSP10, EPAS1, ERRFI1, FBXO32, FLJ13611, FN1, GABARAPL1, GBP1, GDAP1, GSN, HIST1H2AE, HIST1H2BD, HLA-DMB, HLA-DQB1, HLA-DRA, HLA-DRB1, HSPA2, IFI27, IFIT1, IFIT3, IL1RAP, KIAA1671, KSR, LARP6, LOC129607, MBP, MCEMP1, MGC14376, MGC19764, MITF, MXRA7, MYO6, NELL2, NGFRAP1L1, OAST, OAS2, PARP12, PARP14, PARP9, PDZK1, PHLDA1, PIK3CD, PLK2, PLSCR1, PRKAR2B, RAB13, RASGEF1B, RSAD2, RTN2, SAT, SCHIP1, SCN3A, SEPP1, SERPINB1, SERPINB9, SERPINI1, SLC27A1, SLC2A14, SLC2A3, SP11O, SSX4, STAT1, STAT4, TJP2, TMPRSS3, TUSC3, USP18, XAF1 and ZCCHC2,
      ii) comparing the ELi of said at least one gene in said biological sample with a predetermined reference level (ELRi),
      iii) calculating a histone acetylation/DNA methylation score (HADMS) using the formula $$HADMS = \sum_{i=1}^{n} \beta i \times Ci$$

wherein βi represent the regression β coefficient reference value for the gene $G_i$ and C=1 if the expression of the gene Gi (ELi) is higher than the predetermined reference level (ELRi) or Ci=-1 if the expression of the gene (ELi) is lower than or equal to the predetermined reference level (ELRi), and iv) comparing said HADMS with a predetermined HADMS reference value ($HADMS_R$),
v) confirming that said HADMS is higher than said $HADMS_R$ and concluding that said patient is able to respond to said combination treatment, and
b) administering to said patient an effective amount of said combination treatment consisting of at least one histone deacetylase inhibitor (HDACi) with at least one DNA methyltransferase inhibitor (DNMTi).

2. The method of claim 1, wherein said biological sample is at least one cell.

3. The method of claim 2, wherein said at least one cell is selected from the group consisting of a multiple myeloma cell, a plasma cell, a bone marrow cell and a medullary cell.

4. The method of claim 1, wherein said at least one HDACi is selected from the group consisting of panobinostat (LBH-589), trichostatin-A (TSA), vorinostat (SAHA), belinostat (PXD101), NVP-LAQ824, givinostat (ITF2357), romidepsin, depsipeptide, aliphatic acids, valproic acid (VPA), and sodium phenylbutyrate.

5. The method of claim 1, wherein said at least one DNMTi is selected from the group consisting of 5-Azacytidine (azacytidine), 5-Aza-2'-deoxycytidine (decitabine, 5-Aza-CdR), zebularine, 5-Fluoro-2'-deoxycytidine (5-F-CdR), 5,6-Dihydro-5-azacytidine (DHAC), hydralazine, Procainamide, procaine, EGCG ((−)-epigallocatechin-3-gallate), and psammaplin A.

6. The method according to claim 1, wherein the measuring of the Eli is carried out for 42 genes selected from the group consisting of: EPAS1, ATP1B1, TJP2, RAB13, IFI27, PLSCR1, CYP1B1, SLC2A3, IFIT1, SCHIP1, PDZK1, DDR1, HLA-DRA, SERPINB9, SP110, SSX4, C1orf38, FN1, MXRA7, CLIC5, HIST1H2AE, MGC14376, HLA-DRB1, SLC2A14, USP18, DKFZp434C0328, CDC14B, DDX58, PARP9, TMPRSS3, COTL1, PARP14, KIAA1671, GDAP1, LOC129607, SLC27A1, FLJ13611, KSR, HIST1H2BD, BIRC4BP and RSAD2.

7. The method according to claim 1, wherein the measuring of the Eli is carried out for 93 genes selected from the group consisting of: ABCB1, ADAM28, ADFP, ANK3, ARRDC4, ATP1B1, BIRC4BP, C11orf32, C1orf38, CD24, CDC14B, CDC42EP3, CDH1, CDKN1A, CDKN1C, CFH, CLIC5, COTL1, CT45-2, CYP1B1, DDR1, DDX58, DHRS2, DKFZp434C0328, DUSP10, EPAS1, ERRFI1, FBXO32, FLJ13611, FN1, GABARAPL1, GBP1, GDAP1, GSN, HIST1H2AE, HIST1H2BD, HLA-DMB, HLA-DQB1, HLA-DRA, HLA-DRB1, HSPA2, IFI27, IFIT1, IFIT3, IL1RAP, KIAA1671, KSR, LARP6, LOC129607, MBP, MCEMP1, MGC14376, MGC19764, MITF, MXRA7, MYO6, NELL2, NGFRAP1L1, OAS1, OAS2, PARP12, PARP14, PARP9, PDZK1, PHLDA1, PIK3CD, PLK2, PLSCR1, PRKAR2B, RAB13, RASGEF1B, RSAD2, RTN2, SAT, SCHIP1, SCN3A, SEPP1, SERPINB1, SERPINB9, SERPINI1, SLC27A1, SLC2A14, SLC2A3, SP11O, SSX4, STAT1, STAT4, TJP2, TMPRSS3, TUSC3, USP18, XAF1 and ZCCHC2.

8. The method of claim 1,
wherein said at least one HDACi is selected from the group consisting of panobinostat (LBH-589), trichostatin-A (TSA), vorinostat (SAHA), belinostat (PXD101), NVP-LAQ824, givinostat (ITF2357), romidepsin, depsipeptide, aliphatic acids, valproic acid (VPA), sodium phenylbutyrate, and
wherein said at least one DNMTi is selected from the group consisting of 5-Azacytidine (azacytidine), 5-Aza-2'-deoxycytidine (decitabine, 5-Aza-CdR), zebularine, 5-Fluoro-2'-deoxycytidine (5-F-CdR), 5,6-

Dihydro-5-azacytidine (DHAC), hydralazine, procainamide, procaine, EGCG ((−)-epigallocatechin-3-gallate), and psammaplin A.

\* \* \* \* \*